(12) United States Patent
Cywin et al.

(10) Patent No.: US 7,291,733 B2
(45) Date of Patent: Nov. 6, 2007

(54) SUBSTITUTED TRICYCLIC HETEROCYCLES AND THEIR USES

(75) Inventors: Charles Lawrence Cywin, Bethel, CT (US); Roman Wolfgang Fleck, Greenwich, CT (US); Eugene Richard Hickey, Danbury, CT (US); Weimin Liu, Sandy Hook, CT (US); Tina Marie Morwick, New Milford, CT (US); John Robert Proudfoot, Newtown, CT (US); Denice M. Spero, West Redding, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 327 days.

(21) Appl. No.: 10/960,550

(22) Filed: Oct. 7, 2004

(65) Prior Publication Data

US 2005/0101601 A1    May 12, 2005

Related U.S. Application Data

(60) Provisional application No. 60/510,160, filed on Oct. 10, 2003.

(51) Int. Cl.
*C07D 491/00* (2006.01)
*C07D 498/00* (2006.01)
*C07D 513/00* (2006.01)
*C07D 515/00* (2006.01)

(52) U.S. Cl. ..................................................... 546/83
(58) Field of Classification Search .................... None
See application file for complete search history.

(56) References Cited

U.S. PATENT DOCUMENTS

| | | | |
|---|---|---|---|
| 4,239,887 | A | 12/1980 | Youssefyeh et al. |
| 6,964,956 | B2 | 11/2005 | Chen et al. |
| 2002/0151544 | A1 | 10/2002 | Hayakawa et al. |
| 2004/0180922 | A1 | 9/2004 | Cywin et al. |
| 2005/0038104 | A1 | 2/2005 | Chen et al. |
| 2005/0182053 | A1 | 8/2005 | Chen et al. |

FOREIGN PATENT DOCUMENTS

| | | |
|---|---|---|
| WO | WO95/19970 | 7/1995 |
| WO | WO 01/68648 | 9/2001 |

OTHER PUBLICATIONS

Baker, S., et al, Synthesis of Pyridine Fused Polycyclic Amines Using Sequential Ring-closing Metathesis and Radical Cyclisation Reactions, Tetrahedron Letters, 44, 2995-2999 (2003).*
J. M. Quintela, et al. "Synthesis and Antiallergic Activity of Pyridothienopyrimidines", Bioorganic & Medicinal Chemistry, vol. 6, 1998, pp. 1911-1925.
T.S. Shah, et al. "Pharmacological Evaluation of LM-2616: A Beta1-Adrenoceptor Antagonist with Beta2-Adrenoceptor Agonistic Activity", Pharm. Comm. 1995, vol. 5, pp. 253-265.
J.M. Quintela, et al. "Synthesis, antihistaminic and cytotoxic activity of pyridothieno- and pyridodithienotriazines", Eur. J. Med. Chem. vol. 33, 1998, pp. 887-897.
F. Guerrera, et al. "Synthesis and Antifungal Activity of Pyrido[3',2':4,5]Thieno[3,2-d]-1,2,3-Triazine Derivatives", Il Farmaco, vol. 48, No. 12, pp. 1725-1733, 1993.
A. Baba, et al. "Studies on Disease-Modifying Antirheumatic Drugs. IV. 1) Synthesis of novel Thieno[2,3-b : 5,4-c']dipyridine derivatives and Their Anti-inflammatory Effect", Chem. Pharm. Bull. vol. 47, No. 7, pp. 993-999, 1999.
G.Wagner, et al., "Synthese von acylierten 4-hydrazino-pyrido[3',2':4,5]thieno[3,2-d] pyrimidinen und tetracyclischen Verbindungen gleicher tricyclischer Grundstruktur und einem am Pyrimidinring anellierten heterocyclus" , Pharmazie, vol. 48, 1993, pp. 20-23.
K.G. Dave, et al., "Reaction of Nitriles under Acidic Conditions, Part I. A General Method of Synthesis of Condensed Pyrimidines", J. Heterocyclic Chem. vol. 17, 1980, pp. 1497-1500.
V.A. Artyomov, et al., "N-Cyanochloroacetamidine—a Convenient Reagent for the Regioselective Synthesis of Fused Diaminopyrimidines", Tetra. vol. 52, No. 3, pp. 1011-1026, 1996.

* cited by examiner

*Primary Examiner*—Zachary C. Tucker
*Assistant Examiner*—Erich A. Leeser
(74) *Attorney, Agent, or Firm*—Michael Morris; Mary-Ellen M. Devlin; David Dow

(57) ABSTRACT

Disclosed are substituted tricyclic heterocycle compounds of the formulas (I), (II) and (III) shown below, wherein $R_1$, $R_2$, $R_3$ and $R_4$ are described herein, which are active as anti-inflammatory agents. Also disclosed are methods of using and making such compounds

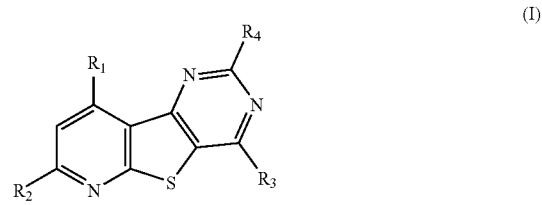

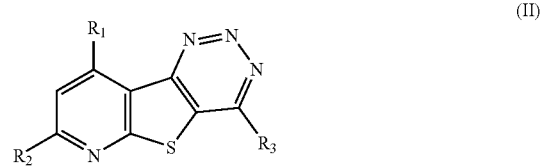

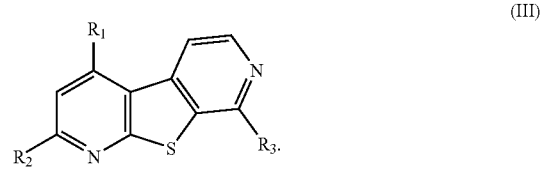

8 Claims, No Drawings

SUBSTITUTED TRICYCLIC HETEROCYCLES AND THEIR USES

APPLICATION DATA

This application claims benefit to U.S. provisional application No. 60/510,160 filed Oct. 10, 2003.

FIELD OF THE INVENTION

This invention relates to substituted pyrido[3',2':4,5]thieno[3,2-d]pyrimidine, pyrido[3',2':4,5]thieno[3,2-d][1,2,3]triazine and pyrido[3',2':4,5]thieno[3,2-d]pyridine compounds useful as inhibitors of the kinase activity of the IκB kinase (IKK) complex. The compounds are therefore useful in the treatment of IKK-mediated diseases including autoimmune diseases, inflammatory diseases and cancer. The invention also relates to processes for preparing such compounds and pharmaceutical compositions comprising them.

BACKGROUND OF THE INVENTION

NF-κB or nuclear factor κB is a transcription factor that induces the expression of a large number of pro-inflammatory and anti-apoptotic genes. These include cytokines such as IL-1, IL-2, TNF-α and IL-6, chemokines including IL-8 and RANTES, as well as other pro-inflammatory molecules including COX-2 and cell adhesion molecules such as ICAM-1, VCAM-1, and E-selectin. The NF-κB family includes homo- and heterodimeric transcription factors composed of members of the Rel family (see for example P. A. Baeurle and D. Baltimore, *Cell,* 1996, 87, 13). Under resting conditions, NF-κB is present in the cytosol of cells as a complex with IκB. The IκB family of proteins serve as inhibitors of NF-κB, interfering with the function of its nuclear localization signal (see for example U. Siebenlist et al., *Ann. Rev. Cell Biol.,* 1994, 10, 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Upon cellular activation by a variety of pro-inflammatory stimuli including IL-1, TNF-α and LPS (bacterial lipopolysaccharide), two specific serine residues of IκB are phosphorylated. Upon phosphorylation, IκB undergoes polyubiquination and subsequent degradation by the 26S proteasome (see for example V. J. Palombella et al., *Cell,* 1994, 78, 773), freeing NF-κB to translocate to the nucleus. The phosphorylation of IκB is carried out by the IκB kinases (see for example a review by M. Karin and M. Delhase, *Seminars in Immunology,* 2000, 12, 85). The traditional IKK complex includes at least three subunits, IKKα (also called IKK-1), IKKβ (or IKK-2) and IKKγ (or NEMO), although other relevant complexes involving IKKα and IKKβ may exist. IKKα and IKKβ are both catalytic subunits while IKKλ is believed to be a regulatory subunit. Both IKKα and IKKβ can phosphorylate IκB. For the purposes of this document, the terms IKK or IKK complex refers to any complex that has kinase activity derived from IKKα and/or IKKβ subunits.

In vivo, activation of IKK occurs upon phosphorylation of its catalytic subunit. Both IKKα and IKKβ can be phosphorylated on serine residues, S177 and S181 of the activation loop in the case of IKKβ, and S176 and S180 of the activation loop for IKKα. An IKKβ mutant having alanines in place of serines at 177 and 181 prevented IKKβ phosphorylation and subsequent activation of the IKK complex by TNFα, IL-1 and other upstream activators. These results support a key role for IKKβ in phosphorylation of IκB following proinflammatory stimulation.

Studies in which the NF-κB pathway has been inhibited in cells and animals support the concept that inhibition of the phosphorylation of IκB is a viable approach to treatment of inflammatory, autoimmune and other diseases. In these studies, NF-κB activation was prevented by expression of a non-degradable version of the IκB protein. Expression of this inhibitor in synovial cells derived from rheumatoid arthritis patients reduced the expression of TNF-α, IL-6, IL-1β and IL-8 while the anti-inflammatory molecules IL-10, IL-Ira and IL-11 were not affected. Matrix metalloproteinases (MMP1 and MMP3) were also down-regulated (J. Bonderson et al., *Proc. Natl. Acad. Sci. U.S.A.,* 1999, 96, 5668). Transgenic expression of the IκB inhibitor in T cells caused a significant reduction in the severity and onset of collagen-induced arthritis in mice (R. Seetharaman et al., *J. Immunol.* 1999, 163, 1577). These experiments indicate that suppression of NF-κB in the diseased joint could reduce both the severity and progression of RA. In primary intestinal epithelial cells, the NF-κB inhibitor blocked the expression of IL-1, IL-8, iNOS and COX-2, mediators that are up-regulated during the course of inflammatory bowel disease (C. Jubin et al., *J. Immunol.,* 1998, 160, 410). Expression of this inhibitor in certain tumor cells enhances killing of these cells by chemotherapeutic reagents (A. A. Beg and D. Baltimore, *Science,* 274, 782). Collectively, the studies described above provide support that inhibition of NF-κB function through inhibition of IKK may be a useful therapeutic approach to treatment of autoimmune and inflammatory disease, and other diseases including cancer.

These results have been confirmed in mice with targeted disruption of the IKKβ gene. Knockout of the IKKβ gene resulted in embryonic lethality due to apoptosis of hepatocytes. However, fibroblasts from the IKKβ knockouts did not undergo IKK and NF-κB activation upon stimulation with IL-1 or TNFα (Q. Li et al., *Science,* 1999, 284, 321), supporting a key role for IKKβ in and NF-κB activation following inflammatory stimuli.

A conditional knockout was generated by expressing a liver-specific inducible dominant negative IκBβ transgene (I. Lavon et al., *Nature Medicine,* 2000, 6, 573). These mice were viable with no signs of liver dysfunction even after one year but they did have impaired immune function. This study supports the idea that inhibition of IKKβ can result in immune suppression without damage to the liver.

IKKα knockout mice died shortly after birth and displayed a variety of skeletal defects and skin abnormalities. Fibroblast and thymocytes from these mice showed normal IKK activation and IκB degradation in response to TNFα, IL-1 or LPS (Y. Hu et al., *Science,* 1999, 284, 316; K. Takeda et al., *Science,* 1999, 284, 313). Recent studies with knockout and knockin mice have revealed distinct roles for IKKα in development and cell signaling. In contrast to the studies with IKKα knockout mice, mice having a kinase inactive version of IKKα knocked in are viable and fertile, indicating that the perinatal lethality and abnormalities seen in the IKKα knockout mice are not due to the lack of kinase activity. However, these mice do have defects in B cell maturation and development of secondary lymphoid organs (U. Senftleben et al., *Science,* 2001, 293, 1495). This phenotype appears to be due to a defect in processing of the NF-κB2/p 10 protein to p52, the DNA binding form of this member of the Rel family of transcription factors. In turn, this leads to a defect in the activation of a subset of NF-κB target genes in B cells. In addition, other studies with these same mice have shown that IKKα kinase activity is required for NF-κB activation in the mammary epithelium during pregnancy (Cao, Y., et. al., *Cell*, 2001, 107,763). This pathway is specifically activated through the TNF receptor family member RANK, requires phosphorylation of the canonical IKK substrate IκBα, and culminates in induction of the cell cycle regulatory gene Cyclin D1.

These studies indicate that an inhibitor of IKKα kinase activity may be useful in treating diseases associated with inappropriate B cell activation such as lupus (O. T. Chan et al., *Immunological Rev.*, 1999, 169, 107) and rheumatoid arthritis (A. Gause and C. Borek, *Biodrugs*, 2001, 15, 73). In addition, an inhibitor of IKKα may be useful in the treatment of breast cancer since NF-κB is constitutively active in a number of breast tumors and many of these tumors depend on Cyclin D1 for proliferation.

Some inhibitors of IKKβ have been reported. WO 01/58890 describes heteoaromatic carboxamide derivatives as inhibitors of IKKβ. WO 01/68648 describes substituted β-carbolines having IKKβ inhibiting activity. Substituted indoles having IKKβ inhibitory activity are reported in WO 01/30774. WO 01/00610 describes substituted benzimidazoles having NF-κB inhibitory activity. Aspirin and salicylate have been reported to bind to and inhibit IKKβ (M. Yin et al., *Nature*, 1998, 396, 77).

Substituted pyrido[3',2':4,5]thieno[3,2-d]pyrimidines having PI3K inhibiting activity are reported in US 2002/0151544 A1. A. J. Bridges described a fused tricylic system, including pyrido[3',2':4,5]thieno[3,2-d]pyrimidines in the broadest sense, as tyrosine kinase inhibitors (WO9519970). Similarly, J. P. Daub also described a fused ring system, in its broad form encompassing pyrido[3',2':4,5]thieno[3,2-d]pyrimidines, as fungicides (WO9314080). J. M. Quitela et al (*Bioorg. Med. Chem.*, 1998, 6, 1911) reported that certain substituted pyrido[3',2':4,5]thieno[3,2-d]pyrimidines could induce or inhibit the release of histamine from rat mast cells. LM-2616, 2,7,9-trimethyl-4-(N-methyl-piperazino)pyrido[3',2':4,5]-thieno[3,2-d]pyrimidine, was reported by T. S. Shah et al. as a beta-1 adrenoceptor antagonist and a beta-2 adrenoceptor agonist (*Pharm. Comm.* 1995,5, 253). Possible antimicrobial activity of compounds with this core structure was reported by J. M. Michael et al. (Al-Azhar, Bull. Science, 1992, 3, 767).

A number of substituted pyrido[3',2':4,5]thieno[3,2-d]pyrimidines have been described in the chemical literature. Examples include 9-(3-pyridinyl)-pyrido[3',2':4,5]thieno[3,2-d]pyrimidine-2,4-diamine, 9-(2-furanyl)-7-phenyl-pyrido[3',2':4,5]thieno[3,2-d]pyrimidin -4-amine, 9-(4-fluorophenyl)-7-(2-thienyl)-pyrido[3',2':4,5]thieno[3,2-d]pyrimidine -2,4-diamine monohydrobromide, 1-(4-amino-7-methylpyrido[3',2':4,5]thieno[3,2-d]pyrimidin -8-yl)-ethanone, 7-butyl-pyrido[3',2':4,5]thieno[3,2-d]pyrimidin-4-amine, 9-(4-chlorophenyl)-7-(2-thienyl)-pyrido[3',2':4,5]thieno[3,2-d]pyrimidin-4-amine, 9-phenyl-7-(2-thienyl)-pyrido[3',2':4,5]thieno[3,2-d]pyrimidin-4-amine, 9-(2-chlorophenyl)-7-(2-thienyl) -pyrido[3',2':4,5]thieno[3,2-d]pyrimidin-4-amine, 7,9-diphenyl-pyrido[3',2':4,5]thieno[3,2-d]pyrimidin-4-amine, 7-(4-methoxyphenyl)-9-phenyl-pyrido[3',2':4,5]thieno[3,2-d]pyrimidin-4-amine, 9-methyl-7-phenyl-pyrido[3',2':4,5]thieno[3,2-d]pyrimidin-4-amine, 7-(2-thienyl)-9-(trifluoromethyl)-pyrido[3',2':4,5]thieno[3,2-d]pyrimidine-2,4-diamine, 7-(4-methoxyphenyl)-9-(trifluoromethyl)-pyrido[3',2':4,5]thieno[3,2-d]pyrimidin-4-amine, 9-(4-chlorophenyl)-7-(2-thienyl)-pyrido[3',2':4,5]thieno[3,2-d]pyrimidine-2,4-diamine, 9-(4-fluorophenyl)-7-(2-thienyl)-pyrido[3',2':4,5]thieno[3,2-d]pyrimidine-2,4-diamine, 7-(2-thienyl)-pyrido[3',2':4,5]thieno[3,2-d]pyrimidine-2,4-diamine, 9-phenyl-7-(2-thienyl) -pyrido[3',2':4,5]thieno[3,2-d]pyrimidine-2,4-diamine, 7-phenyl-pyrido[3',2':4,5]thieno[3,2-d]pyrimidin-4-amine, 1-(2,4-diamino-7-methylpyrido[3',2':4,5]thieno[3,2-d]pyrimidin-8-yl)-ethanone, 2,4,7-triamino-pyrido[3',2':4,5]thieno[3,2-d]pyrimidine-8-carbonitrile, 7-methyl-9-(trifluoromethyl)-pyrido[3',2':4,5]thieno[3,2-d]pyrimidin-4-amine, 7,9-di-2-thienyl-pyrido[3',2':4,5]thieno[3,2-d]pyrimidine-2,4-diamine, 7-ethyl-8-methyl -pyrido[3',2':4,5]thieno[3,2-d]pyrimidin-4-amine, 7,8,9-trimethyl-pyrido[3',2':4,5]thieno[3,2-d]pyrimidin-4-amine, 7-(2-methylpropyl)-pyrido[3',2':4,5]thieno[3,2-d]pyrimidin-4-amine, 7-methyl-pyrido[3',2':4,5]thieno[3,2-d]pyrimidin-4-amine, 7-cyclopropyl-9-(4-methoxyphenyl)-pyrido[3',2':4,5]thieno[3,2-d]pyrimidin-4-amine, 9-(2,4-dichlorophenyl)-7-(2-thienyl)-pyrido[3',2':4,5]thieno[3,2-d]pyrimidin-4-amine, 7-methyl-9-(trifluoromethyl) -pyrido[3',2':4,5]thieno[3,2-d]pyrimidine-2,4-diamine, 4,7-diamino-9-methyl -pyrido[3',2':4,5]thieno[3,2-d]pyrimidine-8-carbonitrile, 2-amino-7-ethoxy-9-phenyl -pyrido[3',2':4,5]thieno[3,2-d]pyrimidine-8-carbonitrile, 2,4,7-triamino-9-(methylthio) -pyrido[3',2':4,5]thieno[3,2-d]pyrimidine-8-carbonitrile, 9-(2-furanyl)-7-methyl -pyrido[3',2':4,5]thieno[3,2-d]pyrimidine-2,4-diamine, 7-propyl-pyrido[3',2':4,5]thieno [3,2-d]pyrimidine-4-amine, 8-ethyl-7-methyl-pyrido[3',2':4,5]thieno[3,2-d]pyrimidin-4-amine, 7,9-bis(trifluoromethyl)-pyrido[3',2':4,5]thieno[3,2-d]pyrimidine-2,4-diamine, 7-phenyl-9-(trifluoromethyl)-pyrido[3',2':4,5]thieno[3,2-d]pyrimidine-2,4-diamine, 7-phenyl -pyrido[3',2':4,5]thieno[3,2-d]pyrimidine-2,4-diamine, 7,9-dimethyl -pyrido[3',2':4,5]thieno[3,2-d]pyrimidine-2,4-diamine, 7-methyl-pyrido[3',2':4,5]thieno[3,2-d]pyrimidine-2,4-diamine, 9-(4-chlorophenyl)-7-(4-methylphenyl) -pyrido[3',2':4,5]thieno[3,2-d]pyrimidine-2,4-diamine, 7,9-diphenyl -pyrido[3',2':4,5]thieno[3,2-d]pyrimidine-2,4-diamine, 4-amino-6,7-dihydro-7-oxo-9-phenyl -pyrido[3',2':4,5]thieno[3,2-d]pyrimidine-8-carbonitrile, 7-(3-pyridinyl) -pyrido[3',2':4,5]thieno[3,2-d]pyrimidin-4-amine, 7-phenyl-9-(trifluoromethyl) -pyrido[3',2':4,5]thieno[3,2-d]pyrimidin-4-amine, 7-methyl-9-phenyl -pyrido[3',2':4,5]thieno[3,2-d]pyrimidin-4-amine, 7-(4-methylphenyl)-9-phenyl -pyrido[3',2':4,5]thieno[3,2-d]pyrimidin-4-amine, 7-(4-fluorophenyl)-9-phenyl -pyrido[3',2':4,5]thieno[3,2-d]pyrimidin-4-amine, 7,9-dimethyl-pyrido[3',2':4,5]thieno[3,2-d]pyrimidine-4-amine, 7,9-dimethyl-pyrido[3',2':4,5]thieno[3,2-d]pyrimidin-4-amine.

Some substituted pyrido[3',2':4,5]thieno[3,2-d][1,2,3]triazines were described by J. M. Quintela et al (*Eur. J. Med. Chem.*, 1998, 33, 887) as antihistamines. A number of these compounds were cytotoxic against several human and mouse tumor cell lines. Some other substituted pyrido[3',2':4,5]thieno[3,2-d][1,2,3]triazines with antimicrobial activity were reported by F. Guerrera et al (*Farmaco*, 1993, 48, 1725). D. Y. Raymond described some substituted pyrido[3',2':4,5]thieno[3,2-d][1,2,3]triazines as anti-allergy agents (U.S. Pat. No. 4,239,887). A number of substituted pyrido[3',2':4,5]thieno[3,2-d][1,2,3]triazines were reported in the literature, including: 4-(4-methyl-1-piperazinyl)-7,9-diphenyl-pyrido[3',2':4,5]thieno[3,2-d]-1,2,3-triazine, 1-[4-[4-(7,9-diphenylpyrido[3',2':4,5]thieno[3,2-d]-1,2,3-triazin-4-yl)-1-piperazinyl]phenyl]-ethanone, N-(4-morpholinylmethyl)-pyrido[3',2':4,5]thieno[3,2-d]-1,2,3-triazin-4-amine, N-methyl-pyrido[3',2':4,5]thieno[3,2-d]-1,2,3-triazin-4-amine, N -butyl-7-methyl-4-(1-piperidinyl)-pyrido[3',2':4,5]thieno[3,2-d]-1,2,3-triazine-9-carboxamide, N-butyl-4-[[(2-chlorophenyl)methyl]amino]-7-methyl -pyrido[3',2':4,5]thieno[3,2-d]-1,2,3-triazine-9-carboxamide, N-butyl-4-[[2-

(diethylamino)ethyl]amino]-7-methyl-pyrido[3',2':4,5] thieno[3,2-d]-1,2,3-triazine-9-carboxamide, N-butyl-4-(butylamino)-7-methyl-pyrido[3',2':4,5]thieno[3,2-d]-1,2,3-triazine-9-carboxamide, 2-[[7-methyl-9-(4-pyridinyl)pyrido[3',2':4,5]thieno[3,2-d]-1,2,3-triazin-4-yl]amino]-ethanol, 2-[[7-methyl-9-(3-pyridinyl)pyrido[3',2':4,5]thieno[3,2-d]-1,2,3-triazin-4-yl]amino]-ethanol, N,N-dimethyl-N'-[7-methyl-9-(4-pyridinyl)pyrido[3',2':4,5]thieno[3,2-d]-1,2,3-triazin-4-yl]-1,2-ethanediamine, N,N -dimethyl-N'-[7-methyl-9-(3-pyridinyl)pyrido[3',2':4,5]thieno[3,2-d]-1,2,3-triazin-4-yl]-1,2-ethanediamine, 9-(4-chlorophenyl)-7-phenyl-4-(1-piperidinyl)-pyrido[3',2':4,5]thieno[3,2-d]-1,2,3-triazine, 7-methyl-N-[3-(4-morpholinyl)propyl]-pyrido[3',2':4,5] thieno[3,2-d]-1,2,3-triazin-4-amine, 7-methyl-pyrido[3',2': 4,5]thieno[3,2-d]-1,2,3-triazine, 7-methyl -pyrido[3',2':4,5] thieno[3,2-d]-1,2,3-triazin-4(1H)-one (1-methylethylidene) hydrazone, 2-(7-methylpyrido[3',2':4,5]thieno[3,2-d]-1,2,3-triazin-4-yl)-hydrazinecarboxylic acid methyl ester, 7-methyl-pyrido[3',2':4,5]thieno[3,2-d]-1,2,3-triazin-4-amine, and N,7-dimethyl -pyrido[3',2':4,5]thieno[3,2-d]-1,2, 3-triazin-4-amine.

Substituted pyrido[3',2':4,5]thieno[3,2-d][1,2,3]pyridines have been reported in the literature (Baba et al, *Chem. Pharm. Bull.*, 1999, 47, 993).

SUMMARY OF THE INVENTION

It is therefore an object of this invention to provide novel compounds according to the following formulas (I) and (II) and (III):

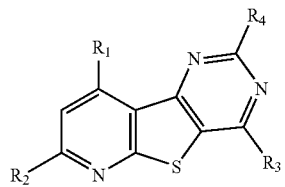

(I)

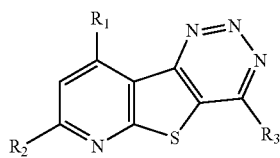

(II)

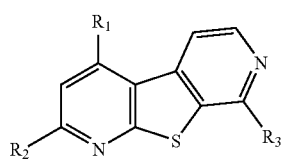

(III)

wherein the variables $R_1$, $R_2$, $R_3$, and $R_4$ are described herein, which inhibit IKK. It is a further object of the invention to provide methods for treating diseases and pathological conditions exacerbated by IKK such as, but not limited to autoimmune diseases, inflammatory diseases and cancer. It is yet a further object of the invention to provide novel processes for preparation of the above-mentioned novel compounds.

DETAILED DESCRIPTION OF THE INVENTION

A first embodiment of the invention comprises a compound of formula (I)

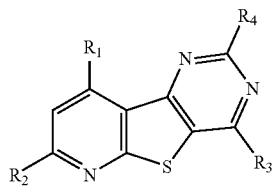

(I)

wherein:

$R_1$ is (a) phenyl or heteroaryl selected from furanyl, thienyl, pyridyl, pyrrolyl, imidazolyl and benzofuranyl, optionally substituted with one to two $R_a$, (b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl, (c) $R_b(CH_2)_mO$—, (d) $C_{3-6}$-cycloalkyl, (e) $C_{3-6}$-cycloalkyl$C_{1-3}$alkyl (f) $R_bOCH_2$—, (g) $R_b(CH_2)_mNH$—, (h) $R_b(CH_2)_p(CH=CH)_m$—, (i) $C_{1-6}$alkyl, (j) $C_{1-8}$alkoxy, (k) $C_{1-8}$alkylthio, (l) $C_{1-6}$alkoxy$C_{1-6}$alkoxy, (m) —$CF_3$, (n) —CHO, (o) —$OCH_2CO_2H$, (p) —$OSO_2CF_3$, (q) —$N(R_c)(R_d)$, or (r) —$C(O)NR_cR_d$;

$R_2$ is (a) $C_{1-6}$alkyl-OC(O)$C_{1-6}$alkoxy, (b) hydroxy$C_{1-6}$alkyl-, (c) hydroxy$C_{1-6}$alkoxy-, optionally substituted with —C(O)$C_{1-6}$alkyl, (d) $(R_c)(R_d)NC_{1-6}$alkoxy-, (e) $(R_c)(R_d)NC_{1-6}$alkyl-, (f) hydroxy$C_{1-6}$alkylamino-, (g) $(R_c)(R_d)NC_{1-6}$alkylamino-, (h) $C_{1-6}$alkoxy$C_{1-6}$alkylamino-, (i) heterocyclyl$(CH_2)_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$, (j) heterocyclyl$(CH_2)_mO$— wherein the heterocyclyl is selected from 1-piperidinyl, 1-piperazinyl, 4-morpholinyl and 1-pyrrolidinyl, optionally substituted with $C_{1-6}$alkyl, (k) $R_b(CH_2)_mO$—,
(l) heteroaryl$(CH_2)_mO$—, wherein the heteroaryl is selected from furanyl, thienyl, imidazolyl, pyridyl, indolyl and pyrrolyl,
(m) heteroaryl$C_{1-6}$alkylamino, wherein the heteroaryl is selected from furanyl, thienyl, imidazolyl, pyridyl, indolyl and pyrrolyl,
(n) —S$C_{1-6}$alkyl, or
(o) —S$C_{1-6}$alkylC(O)N($R_c$)($R_d$);

$R_3$ is —N($R_c$)($R_d$);
$R_4$ is hydrogen or —NH$_2$;
$R_a$ is chosen from $C_{1-6}$alkyl, $C_{1-6}$alkoxy, hydroxy$C_{1-6}$alkyl, halogen, —CN, —CO$_2$H, —CO$_2C_{1-6}$alkyl, —S(O)$_nC_{1-6}$alkyl, —NO$_2$, —OH, —CF$_3$, —N($R_c$)($R_d$), —NHC(O)NHC$_{1-6}$alkyl, —C(O)N($R_c$)($R_d$) and phenyl optionally substituted with halogen, $C_{1-6}$alkyl, —CN or $C_{1-6}$alkoxy;
$R_b$ is a phenyl group optionally substituted with one or two groups selected from halogen, pyridyl, $C_{1-6}$alkyl, —CN, —CO$_2C_{1-6}$alkyl, —C(O)N($R_c$)($R_d$), NO$_2$ and $C_{1-6}$alkoxy, or $R_b$ is $C_{3-6}$cycloalkyl, naphthyl, pyridyl, quinolinyl and isoquinolinyl;
$R_c$ and $R_d$ are independently selected from H, $C_{1-6}$alkyl, —C(O)$C_{1-6}$alkyl, —SO$_2C_{1-6}$alkyl, phenyl, benzyl, piperidinyl, phenylethyl and (CH$_3$)$_3$COC(O)—, and wherein if $R_c$ and $R_d$ are both $C_{1-6}$alkyl, they may optionally form a 4-7 member ring, together with the nitrogen they are attached to;
$R_e$ is selected from —OH,NHCHO, —O(CH$_2$)phenyl, amino, —CN, oxo-CO$_2C_{1-6}$alkyl, —CO$_2$H, —C(O)N($R_c$)($R_d$), N($R_c$)($R_d$), —CH$_2$N($R_c$)($R_d$), —NHCH$_2$CO$_2$H, —NHCH$_2$CO N($R_c$)($R_d$), —NHCOObenzyl, $C_{1-6}$alkyl, —CO$_2$benzyl, hydroxy$C_{1-6}$alkyl, —C(O)$C_{1-6}$alkylN($R_c$)($R_d$), —NHCO$_2C_{1-6}$alkyl, HOCH($R_g$)CH$_2$NH—, —NHC(O)N($R_c$)($R_d$), —S(O)$_nC_{1-6}$alkyl, (CH$_3$)$_3$COC(O)—, phenyl, pyridyl, H$_2$NCH($R_f$)C(O)— and —C(O)heterocyclyl, wherein said heterocyclyl is selected from piperidinyl, piperazinyl, morpholinyl and pyrrolidinyl;
$R_f$ is selected from $C_{1-6}$alkyl, —(CH$_2$)$_{1-4}$NH$_2$, benzyl or $R_b$;
$R_g$ is $C_{1-6}$alkyl, an aryl or a heteroaryl group selected from phenyl, naphthyl, imidazolyl, thienyl, thiazolyl, pyridyl, pyrimidyl, pyrazinyl, benzothiophenyl, benzothiazolyl, indolyl, benzimidazoyl, quinolinyl, isoquinolinyl, benzo[1,3]dioxoly, 2,3-dihydro -benzo[1,4]dioxinyl, 1-oxo-1,3-dihydro-isobenzofuranyl, 2,3-dihydro-benzofuranyl, 3-oxo -3,4-dihydro-2H-benzo[1,4]oxazinyl and 2-oxo-2,3-dihydro-benzooxazoly,
$R_g$ is optionally substituted with one to three $R_h$ groups selected from halogen, hydroxyl, $C_{1-6}$alkyl, benzyl, $C_{1-6}$alkoxy, phenoxy, phenylamino, hydroxy$C_{1-6}$alkyl, —CN, —CO$_2$H, —CO$_2C_{1-6}$alkyl, —N($R_c$)($R_d$), $C_{1-6}$alkylN($R_c$)($R_d$), —C(O)N($R_c$)($R_d$), —NO$_2$, —S(O)$_nC_{1-6}$alkyl and —S(O)$_n$N($R_c$)($R_d$), or $R_h$ is an aryl or a heteroaryl group selected from phenyl, imidazolyl, pyrazolyl, thienyl, oxazoly, thiazolyl, pyridyl, pyrimidyl, pyrazinyl, benzo[1,3]dioxoly, and quinolinyl, or $R_h$ is morpholinyl,
$R_h$ is optionally substituted with one to three $R_i$ groups selected from halogen, hydroxyl, $C_{1-6}$alkyl, $C_{1-6}$alkoxy, —CN, —CO$_2$H, —CO$_2C_{1-6}$alkyl, —N($R_c$)($R_d$) and C(O)N($R_c$)($R_d$);
m is 0 or 1;
n is 0, 1 or 2; and
p is 0, 1, 2 or 3;

or the pharmaceutically acceptable salts, esters, isomers or tautomers thereof.

A second embodiment of the invention comprises a compound of formula (I) as described in the first embodiment above wherein:
$R_1$ is
(a) phenyl or heteroaryl selected from furanyl, thienyl, pyridyl, pyrrolyl, imidazolyl and benzofuranyl, optionally substituted with one to two $R_a$,
(b) heterocyclyl selected from 1-piperidinyl, 1-piperazinyl, 1-pyrrolidinyl and 4-morpholinyl, optionally substituted with one to two groups selected from $C_{1-6}$alkyl, —CO$_2C_{1-5}$alkyl, phenyl, benzyl, —OH and —C(O)heteroaryl, wherein the heteroaryl is selected from furanyl, thienyl, pyridyl and pyrrolyl,
(c) $R_b(CH_2)_mO$—,
(d) $C_{3-6}$-cycloalkyl,
(e) $C_{3-6}$-cycloalkyl$C_{1-3}$alkyl
(f) $R_bOCH_2$—,
(g) $R_b(CH_2)_mNH$—,
(h) $R_b(CH_2)_p(CH=CH)_m$—
(i) $C_{1-6}$alkyl,
(j) $C_{1-6}$alkoxy,
(k) $C_{1-8}$alkylthio,
(l) $C_{1-6}$alkoxy$C_{1-6}$alkoxy,
(m) —CF$_3$,
(n) —CHO,
(o) —OCH$_2$CO$_2$H,
(p) —OSO$_2$CF$_3$,
(q) —N($R_c$)($R_d$), or
(r) —C(O)NR$_c$R$_d$;
$R_2$ is
(a) $C_{1-6}$alkyl-OC(O)$C_{1-6}$alkoxy,
(b) hydroxy$C_{1-6}$alkyl-,
(c) hydroxy$C_{1-6}$alkoxy-, optionally substituted with —C(O)$C_{1-6}$alkyl,
(d) ($R_c$)($R_d$)NC$_1$alkoxy-,
(e) ($R_c$)($R_d$)N$C_{1-6}$alkyl-,
(f) hydroxy$C_{1-6}$alkylamino-,
(g) ($R_c$)($R_d$)N$C_{1-6}$alkylamino-,
(h) $C_{1-6}$alkoxy$C_{1-6}$alkylamino-,
(i) heterocyclyl(CH$_2$)$_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$,
(j) heterocyclylCH$_2$O— wherein the heterocyclyl is selected from 1-piperidinyl, 1-piperazinyl, 4-morpholinyl and 1-pyrrolidinyl, optionally substituted with $C_{1-6}$alkyl,
(k) $R_b(CH_2)_mO$—,
(l) heteroaryl(CH$_2$)$_mO$—, wherein the heteroaryl is selected from furanyl, thienyl, imidazolyl, pyridyl, indolyl and pyrrolyl,
(m) heteroaryl$C_{1-6}$alkylamino, wherein the heteroaryl is selected from furanyl, thienyl, imidazolyl, pyridyl, indolyl and pyrrolyl,
(n) —S$C_{1-6}$alkyl, or
(o) —S$C_{1-6}$alkylC(O)N($R_c$)($R_d$);
$R_3$ is —N($R_c$)($R_d$);
$R_4$ is hydrogen or —NH$_2$;
$R_a$ is chosen from $C_{1-6}$alkyl, $C_{1-6}$alkoxy, hydroxy$C_{1-6}$alkyl, halogen, —CN, —CO$_2$H, —CO$_2C_{1-6}$alkyl, —S(O)$_nC_{1-6}$alkyl, —NO$_2$, —OH, —CF$_3$, —N($R_c$)($R_d$), —NHC(O)NHC$_{1-6}$alkyl, —C(O)N($R_c$)($R_d$) and phenyl optionally substituted with halogen, $C_{1-6}$alkyl, —CN or $C_{1-6}$alkoxy;
$R_b$ is a phenyl group optionally substituted with one or two groups selected from halogen, pyridyl, $C_{1-6}$alkyl, —CN, —CO₂C₁₋₆alkyl, —C(O)N(R_c)(R_d), NO₂ and C₁₋₆alkoxy, or R_b is C₃₋₆cycloalkyl, naphthyl, pyridyl, quinolinyl and isoquinolinyl;

R_c and R_d are independently selected from H, C₁₋₆alkyl, —C(O)C₁₋₆alkyl, —SO₂C₁₋₆alkyl, phenyl, benzyl, piperidinyl, phenylethyl and (CH₃)₃COC(O)—;

R_e is selected from —OH, NHCHO, —O(CH₂)phenyl, amino, —CN, oxo, —CO₂C₁₋₆alkyl, —CO₂H, —C(O)N(R_c)(R_d), —N(R_c)(R_d), —CH₂N(R_c)(R_d), C₁₋₆alkyl, —CO₂benzyl, hydroxyC₁₋₆alkyl, —C(O)C₁₋₆alkylN(R_c)(R_d), —NHCO₂C₁₋₆alkyl, HOCH(R_f)CH₂NH—, —NHC(O)N(R_c)(R_d), —S(O)_nC₁₋₆alkyl, (CH₃)₃COC(O)—, phenyl, pyridyl, H₂NCH(R_b)C(O)— and —C(O)heterocyclyl, wherein said heterocyclyl is selected from piperidinyl, piperazinyl, morpholinyl and pyrrolidinyl;

R_f is selected from C₁₋₆alkyl, —(CH₂)₁₋₄NH₂, phenyl or benzyl;

m is 0 or 1;

n is 0, 1 or 2; and p is 0, 1, 2 or 3;

or the pharmaceutically acceptable salts, esters, isomers or tautomers thereof.

A third embodiment of the invention comprises a compound of formula (I) as described in the embodiment above wherein:

$R_1$ is (a) $C_{1-6}$alkyl, (b) $C_{3-6}$-cycloalkyl, (c) $C_{3-6}$-cycloalkylC$_{1-3}$alkyl (d) $C_{1-4}$alkoxy, (e) $C_{1-4}$alkylthio, (f) —CF₃, or (g) —C(O)N_cR_d;

$R_2$ is heterocyclyl wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two R_e, $R_3$ is —NH₂;

$R_4$ is hydrogen; and

R_c and R_d are independently selected from H, C₁₋₆alkyl, —C(O)C₁₋₆alkyl, —SO₂C₁₋₆alkyl, phenyl, benzyl, piperidinyl, phenylethyl and (CH₃)₃COC(O)—;

R_e is selected from —OH, NHCHO, —O(CH₂)phenyl, amino, —CN, oxo, —CO₂C₁₋₆alkyl, —CO₂H, —C(O)N(R_c)(R_d), —N(R_c)(R_d), —CH₂N(R_c)(R_d), C₁₋₆alkyl, —CO₂benzyl, hydroxyC₁₋₆alkyl, —C(O)C₁₋₆alkylN(R_c)(R_d), —NHCO₂C₁₋₆alkyl, HOCH(R_f)CH₂NH—, —NHC(O)N(R_c)(R_d), —S(O)_nC₁₋₆alkyl, (CH₃)₃COC(O)—, phenyl, pyridyl, H₂NCH(R_f)C(O)— and —C(O)heterocyclyl, wherein said heterocyclyl is selected from piperidinyl, piperazinyl, morpholinyl and pyrrolidinyl;

R_f is selected from C₁₋₆alkyl, —(CH₂)₁₋₄NH₂, phenyl or benzyl;

m is 0 or 1;

n is 0, 1 or 2; and p is 0, 1, 2 or 3;

or the pharmaceutically acceptable salts, esters, isomers or tautomers thereof.

A fourth embodiment of the invention comprises a compound of formula (II)

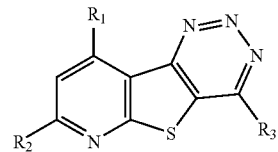

wherein:

$R_1$ is (a) phenyl or heteroaryl selected from furanyl, thienyl, pyridyl, pyrrolyl, imidazolyl and benzofuranyl, optionally substituted with one to two R_a, (b) heterocyclyl selected from 1-piperidinyl, 1-piperazinyl, 1-pyrrolidinyl and 4-morpholinyl, optionally substituted with one to two groups selected from C₁₋₆alkyl, —CO₂C₁₋₅alkyl, phenyl, benzyl, —OH and —C(O)heteroaryl, wherein the heteroaryl is selected from furanyl, thienyl, pyridyl and pyrrolyl, (c) R_b(CH₂)_mO—, (d) C₃₋₆-cycloalkyl, (e) C₃₋₆-cycloalkylC₁₋₃alkyl (f) R_bOCH₂—, (g) R_b(CH₂)_mNH—, (h) R_b(CH₂)_p(CH=CH)_m—

(i) C₁₋₆alkyl, (j) C₁₋₈alkoxy, (k) C₁₋₈alkylthio, (l) C₁₋₆alkoxyC₁₋₆alkoxy, (m) —CF₃, (n) —CHO, (o) —OCH₂CO₂H, (p) —OSO₂CF₃, (q) —N(R_c)(R_d), or (r) —C(O)NR_cR_d;

$R_2$ is (a) C₁₋₆alkyl-OC(O)C₁₋₆alkoxy, (b) hydroxyC₁₋₆alkyl-, (c) hydroxyC₁₋₆alkoxy-, optionally substituted with —C(O)C₁₋₆alkyl, (d) (R_c)(R_d)NC₁₋₆alkoxy-, (e) (R_c)(R_d)NC₁₋₆alkyl-, (f) hydroxyC₁₋₆alkylamino-, (g) (R_c)(R_d)NC₁₋₆alkylamino-, (h) C₁₋₆alkoxyC₁₋₆alkylamino-, (i) heterocyclyl(CH₂)_m— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two R_e, (j) heterocyclyl(CH₂)_mO— wherein the heterocyclyl is selected from 1-piperidinyl, 1-piperazinyl, 4-morpholinyl and 1-pyrrolidinyl, optionally substituted with C₁₋₆alkyl, (k) R_b(CH₂)_mO—, (l) heteroaryl(CH₂)_mO—, wherein the heteroaryl is selected from furanyl, thienyl, imidazolyl, pyridyl, indolyl and pyrrolyl, (m) heteroarylC₁₋₆alkylamino, wherein the heteroaryl is selected from furanyl, thienyl, imidazolyl, pyridyl, indolyl and pyrrolyl, (n) —SC₁₋₆alkyl, or (o) —SC₁₋₆alkylC(O)N(R₄)(R₅);

$R_3$ is —N($R_c$)($R_d$);

$R_a$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —S(O)$_n C_{1-6}$ alkyl, —$NO_2$, —OH, —$CF_3$, —N($R_c$)($R_d$), —NHC(O)NH$C_{1-6}$alkyl, —C(O)N($R_c$)($R_d$) and phenyl optionally substituted with halogen, $C_{1-6}$alkyl, —CN or $C_{1-6}$alkoxy;

$R_b$ is a phenyl group optionally substituted with one or two groups selected from halogen, 1-naphthyl, $C_{1-6}$alkyl, —CN, —$CO_2C_{1-6}$alkyl, —C(O)N($R_c$)($R_d$), $NO_2$ and $C_{1-6}$alkoxy, or $R_b$ is $C_{3-6}$cycloalkyl;

$R_c$ and $R_d$ are independently selected from H, $C_{1-6}$alkyl, —C(O)$C_{1-6}$alkyl, —$SO_2C_{1-6}$alkyl, phenyl, benzyl, piperidinyl, phenylethyl and $(CH_3)_3COC(O)$—, and wherein if $R_c$ and $R_d$ are both $C_{1-6}$alkyl, they may optionally form a 4-7 member ring, together with the nitrogen they are attached to;

$R_e$ is selected from —OH, NHCHO, —O($CH_2$)phenyl, amino, —CN, oxo-$CO_2C_{1-6}$alkyl, —$CO_2H$, —C(O)N($R_c$)($R_d$), N($R_c$)($R_d$), —$CH_2$N($R_c$)($R_d$), —NHCH$_2$CO$_2$H, —NHCH$_2$CO N($R_c$)($R_d$), —NHCOObenzyl, $C_{1-6}$alkyl, —$CO_2$benzyl, hydroxy$C_{1-6}$alkyl, —C(O)$C_{1-6}$alkylN($R_c$)($R_d$), —NHCO$_2C_{1-6}$alkyl, HOCH($R_g$)$CH_2$NH—, —NHC(O)N($R_c$)($R_d$), —S(O)$_n C_{1-6}$alkyl, $(CH_3)_3COC(O)$—, phenyl, pyridyl, $H_2$NCH($R_f$)C(O)— and —C(O)heterocyclyl, wherein said heterocyclyl is selected from piperidinyl, piperazinyl, morpholinyl and pyrrolidinyl;

$R_f$ is selected from $C_{1-6}$alkyl, —$(CH_2)_{1-4}NH_2$, benzyl or $R_b$;

$R_g$ is $C_{1-6}$alkyl, an aryl or a heteroaryl group selected from phenyl, naphthyl, imidazolyl, thienyl, thiazolyl, pyridyl, pyrimidyl, pyrazinyl, benzothiophenyl, benzothiazolyl, indolyl, benzimidazoyl, quinolinyl, isoquinolinyl, benzo[1,3]dioxoly, 2,3-dihydro-benzo[1,4]dioxinyl, 1-oxo-1,3-dihydro-isobenzofuranyl, 2,3-dihydro-benzofuranyl, 3-oxo -3,4-dihydro-2H-benzo[1,4]oxazinyl and 2-oxo-2,3-dihydro-benzooxazoly, $R_g$ is optionally substituted with one to three $R_h$ groups selected from halogen, hydroxyl, $C_{1-6}$alkyl, benzyl, $C_{1-6}$alkoxy, phenoxy, phenylamino, hydroxy$C_{1-6}$alkyl, —CN, —$CO_2H$, —$CO_2C_{1-6}$alkyl, —N($R_c$)($R_d$), $C_{1-6}$alkylN($R_c$)($R_d$), —C(O)N($R_c$)($R_d$), —$NO_2$, —S(O)$_n C_{1-6}$alkyl and —S(O)$_n$N($R_c$)($R_d$), or $R_h$ is an aryl or a heteroaryl group selected from phenyl, imidazolyl, pyrazolyl, thienyl, oxazoly, thiazolyl, pyridyl, pyrimidyl, pyrazinyl, benzo[1,3]dioxoly, and quinolinyl, or $R_h$ is morpholinyl, $R_h$ is optionally substituted with one to three $R_i$ groups selected from halogen, hydroxyl, $C_{1-6}$alkyl, $C_{1-6}$alkoxy, —CN, —$CO_2H$, —$CO_2C_{1-6}$alkyl, —N($R_c$)($R_d$) and C(O)N($R_c$)($R_d$);

m is 0 or 1;

n is 0, 1 or 2; and p is 0, 1, 2 or 3 or the pharmaceutically acceptable salts, esters, isomers or tautomers thereof.

A fifth embodiment of the invention comprises a compound of formula (II) as described in the embodiment above wherein:

wherein:

$R_1$ is (a) phenyl or heteroaryl selected from furanyl, thienyl, pyridyl, pyrrolyl, imidazolyl and benzofuranyl, optionally substituted with one to two $R_a$, (b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl, (c) $R_b(CH_2)_mO$—, (d) $C_{3-6}$-cycloalkyl, (e) $C_{3-6}$-cycloalkyl$C_{1-3}$alkyl (f) $R_aOCH_2$—, (g) $R_b(CH_2)_mNH$—, (h) $R_b(CH_2)_p(CH=CH)_m$—

(i) $C_{1-6}$alkyl, (j) $C_{1-8}$alkoxy, (k) $C_{1-8}$alkylthio, (l) $C_{1-6}$alkoxy$C_{1-6}$alkoxy, (m) —$CF_3$, (n) —CHO, (o) —$OCH_2CO_2H$, (p) —$OSO_2CF_3$, (q) —N($R_c$)($R_d$), or (r) —C(O)NR$_c R_d$;

$R_2$ is (a) $C_{1-6}$alkyl-OC(O)$C_{1-6}$alkoxy, (b) hydroxy$C_{1-6}$alkyl-, (c) hydroxy$C_{1-6}$alkoxy-, optionally substituted with —C(O)$C_{1-6}$alkyl, (d) ($R_c$)($R_d$)N$C_{1-6}$alkoxy-, (e) ($R_c$)($R_d$)N$C_{1-6}$alkyl-, (f) hydroxy$C_{1-6}$alkylamino-, (g) ($R_c$)($R_d$)N$C_{1-6}$alkylamino-, (h) $C_{1-6}$alkoxy$C_{1-6}$alkylamino-, (i) heterocyclyl$(CH_2)_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$, (j) heterocyclyl$CH_2O$— wherein the heterocyclyl is selected from 1-piperidinyl, 1-piperazinyl, 4-morpholinyl and 1-pyrrolidinyl, optionally substituted with $C_{1-6}$alkyl, (k) $R_b(CH_2)_mO$—, (l) heteroaryl$(CH_2)_mO$—, wherein the heteroaryl is selected from furanyl, thienyl, imidazolyl, pyridyl, indolyl and pyrrolyl, (m) heteroaryl$C_{1-6}$alkylamino, wherein the heteroaryl is selected from furanyl, thienyl, imidazolyl, pyridyl, indolyl and pyrrolyl, (n) —S$C_{1-6}$alkyl, or (o) —S$C_{1-6}$alkylC(O)N($R_4$)($R_5$);

$R_3$ is —N($R_c$)($R_d$);

$R_a$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —S(O)$_n C_{1-6}$ alkyl, —$NO_2$, —OH, —$CF_3$, —N($R_c$)($R_d$), —NHC(O)NH$C_{1-6}$alkyl, —C(O)N($R_c$)($R_d$) and phenyl optionally substituted with halogen, $C_{1-6}$alkyl, —CN or $C_{1-6}$alkoxy;

$R_b$ is a phenyl group optionally substituted with one or two groups selected from halogen, 1-naphthyl, $C_{1-6}$alkyl, —CN, —$CO_2C_{1-6}$alkyl, —C(O)N($R_c$)($R_d$), $NO_2$ and $C_{1-6}$alkoxy, or $R_b$ is $C_{3-6}$cycloalkyl;

$R_c$ and $R_d$ are independently selected from H, $C_{1-6}$alkyl, —C(O)$C_{1-6}$alkyl, —$SO_2C_{1-6}$alkyl, phenyl, benzyl, piperidinyl, phenylethyl and $(CH_3)_3COC(O)$—;

$R_e$ is selected from —OH, —$NH_2$, —NHCHO, —O($CH_2$)phenyl, amino, —CN, oxo, —$CO_2C_{1-6}$alkyl, —$CO_2H$, —C(O)N($R_c$)($R_d$), —N($R_c$)($R_d$), —$CH_2$N($R_c$)($R_d$), —$CH_2OH$, $C_{1-6}$alkyl, —$CO_2$benzyl, hydroxy$C_{1-6}$alkyl, —C(O)$C_{1-6}$alkylN($R_c$)($R_d$), —NHCO$_2C_{1-6}$alkyl, HOCH($R_b$)$CH_2$NH—, —NHC(O)N($R_c$)($R_d$), —S(O)$_n C_{1-6}$alkyl, $(CH_3)_3COC(O)$—, phenyl, pyridyl, $H_2$NCH($R_f$)C(O)— and —C(O)heterocyclyl, wherein said heterocyclyl is selected from piperidinyl, piperazinyl, morpholinyl and pyrrolidinyl;

$R_f$ is selected from $C_{1-6}$alkyl, —$(CH_2)_{1-4}NH_2$, phenyl or benzyl;

m is 0 or 1;
n is 0, 1 or 2; and
p is 0, 1, 2 or 3;

and pharmaceutically acceptable derivatives thereof.

A sixth embodiment of the invention comprises a compound of formula (II) as described in the fifth embodiment wherein:

$R_1$ is
(a) $C_{1-6}$alkyl,
(b) $C_{1-4}$alkoxy,
(c) $C_{3-6}$-cycloalkyl,
(d) $C_{3-6}$-cycloalkyl$C_{1-3}$alkyl
(e) $C_{1-4}$alkylthio,
(f) —$CF_3$, or
(g) —$C(O)NR_cR_d$;

$R_2$ is
heterocyclyl wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$;

$R_3$ is —$NH_2$; and $R_c$ and $R_d$ are independently selected from H, $C_{1-6}$alkyl, —$C(O)C_{1-6}$alkyl, —$SO_2C_{1-6}$alkyl, phenyl, benzyl, piperidinyl, phenylethyl and $(CH_3)_3COC(O)$—;

$R_e$ is selected from —OH, —$NH_2$, —NHCHO, —$O(CH_2)$phenyl, amino, —CN, oxo, —$CO_2C_{1-6}$alkyl, —$CO_2H$, —$C(O)N(R_c)(R_d)$, —$N(R_c)(R_d)$, —$CH_2N(R_c)(R_d)$, —$CH_2OH$, $C_{1-6}$alkyl, —$CO_2$benzyl, hydroxy$C_{1-6}$alkyl, —$C(O)C_{1-6}$alkylN$(R_c)(R_d)$, —$NHCO_2C_{1-6}$alkyl, HOCH$(R_b)CH_2NH$—, —$NHC(O)N(R_c)(R_d)$, —$S(O)_nC_{1-6}$alkyl, $(CH_3)_3COC(O)$—, phenyl, pyridyl, $H_2NCH(R_f)C(O)$— and —C(O)heterocyclyl, wherein said heterocyclyl is selected from piperidinyl, piperazinyl, morpholinyl and pyrrolidinyl;

$R_f$ is selected from $C_{1-6}$alkyl, —$(CH_2)_{1-4}NH_2$, phenyl or benzyl;

m is 0 or 1;
n is 0, 1 or 2; and
p is 0, 1, 2 or 3;

or the pharmaceutically acceptable salts, esters, isomers or tautomers thereof.

A seventh embodiment of the invention comprises a compound of formula (III):

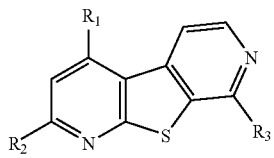

(III)

wherein:
$R_1$ is
(a) phenyl or heteroaryl selected from furanyl, thienyl, pyridyl, pyrrolyl, imidazolyl and benzofuranyl, optionally substituted with one to two $R_a$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
(c) $R_b(CH_2)_mO$—,
(d) $C_{3-6}$-cycloalkyl,
(e) $C_{3-6}$-cycloalkyl$C_{1-3}$alkyl
(f) $R_bOCH_2$—,
(g) $R_b(CH_2)_mNH$—,
(h) $R_b(CH_2)_p(CH=CH)_m$—
(i) $C_{1-6}$alkyl,
(j) $C_{1-8}$alkoxy,
(k) $C_{1-8}$alkylthio,
(l) $C_{1-6}$alkoxy$C_{1-6}$alkoxy,
(m) —$CF_3$,
(n) —CHO,
(o) —$OCH_2CO_2H$,
(p) —$OSO_2CF_3$,
(q) —$N(R_c)(R_d)$, or
(r) —$C(O)NR_cR_d$;

$R_2$ is
(a) $C_{1-6}$alkyl-OC(O)$C_{1-6}$alkoxy,
(b) hydroxy$C_{1-6}$alkyl-,
(c) hydroxy$C_{1-6}$alkoxy-, optionally substituted with —C(O)$C_{1-6}$alkyl,
(d) $(R_c)(R_d)NC_{1-6}$alkoxy-,
(e) $(R_c)(R_d)NC_{1-6}$alkyl-,
(f) hydroxy$C_{1-6}$alkylamino-,
(g) $(R_c)(R_d)NC_{1-6}$alkylamino-,
(h) $C_{1-6}$alkoxy$C_{1-6}$alkylamino-,
(i) heterocyclyl$(CH_2)_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$,
(j) heterocyclyl$CH_2O$— wherein the heterocyclyl is selected from 1-piperidinyl, 1-piperazinyl, 4-morpholinyl and 1-pyrrolidinyl, optionally substituted with $C_{1-6}$alkyl,
(k) $R_b(CH_2)_mO$—,
(l) heteroaryl$(CH_2)_mO$—, wherein the heteroaryl is selected from furanyl, thienyl, imidazolyl, pyridyl, indolyl and pyrrolyl,
(m) heteroaryl$C_{1-6}$alkylamino, wherein the heteroaryl is selected from furanyl, thienyl, imidazolyl, pyridyl, indolyl and pyrrolyl,
(n) —$SC_{1-6}$alkyl, or
(o) —$SC_{1-6}$alkylC(O)$N(R_c)(R_d)$;

$R_3$ is —$N(R_c)(R_d)$;

$R_a$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —$S(O)_nC_{1-6}$alkyl, —$NO_2$, —OH, —$CF_3$, —$N(R_c)(R_d)$, —NHC(O)NH$C_{1-6}$alkyl, —$C(O)N(R_c)(R_d)$ and phenyl optionally substituted with halogen, $C_{1-6}$alkyl, —CN or $C_{1-6}$alkoxy;

$R_b$ is a phenyl group optionally substituted with one or two groups selected from halogen, 1-naphthyl, $C_{1-6}$alkyl, —CN, —$CO_2C_{1-6}$alkyl, —$C(O)N(R_c)(R_d)$, $NO_2$ and $C_{1-6}$alkoxy, or $R_b$ is $C_{3-6}$cycloalkyl;

$R_c$ and $R_d$ are independently selected from H, $C_{1-6}$alkyl, —$C(O)C_{1-6}$alkyl, —$SO_2C_{1-6}$alkyl, phenyl, benzyl, piperidinyl, phenylethyl and $(CH_3)_3COC(O)$—, and wherein if $R_c$ and $R_d$ are both $C_{1-6}$alkyl, they may optionally form a 4-7 member ring, together with the nitrogen they are attached to;

$R_e$ is selected from —OH,NHCHO, —$O(CH_2)$phenyl, amino, —CN, oxo-$CO_2C_{1-6}$alkyl, —$CO_2H$, —$C(O)N(R_c)(R_d)$, $N(R_c)(R_d)$, —$CH_2N(R_c)(R_d)$, —$NHCH_2CO_2H$, —$NHCH_2CO$ $N(R_c)(R_d)$, —NHCOObenzyl, $C_{1-6}$alkyl, —CO$_2$benzyl, hydroxyC$_{1-6}$alkyl, —C(O)C$_{1-6}$alkylN(R$_c$)(R$_d$), —NHCO$_2$C$_{1-6}$alkyl, HOCH(R$_g$)CH$_2$NH—, —NHC(O)N(R$_c$)(R$_d$), —S(O)$_n$C$_{1-6}$alkyl, (CH$_3$)$_3$COC(O)—, phenyl, pyridyl, H$_2$NCH(R$_f$)C(O)— and —C(O)heterocyclyl, wherein said heterocyclyl is selected from piperidinyl, piperazinyl, morpholinyl and pyrrolidinyl;

R$_f$ is selected from C$_{1-6}$alkyl, —(CH$_2$)$_{1-4}$NH$_2$, benzyl or R$_b$;

R$_g$ is C$_{1-6}$alkyl, an aryl or a heteroaryl group selected from phenyl, naphthyl, imidazolyl, thienyl, thiazolyl, pyridyl, pyrimidyl, pyrazinyl, benzothiophenyl, benzothiazolyl, indolyl, benzimidazoyl, quinolinyl, isoquinolinyl, benzo[1,3]dioxoly, 2,3-dihydro-benzo[1,4]dioxinyl, 1-oxo-1,3-dihydro-isobenzofuranyl, 2,3-dihydro-benzofuranyl, 3-oxo-3,4-dihydro-2H-benzo[1,4]oxazinyl and 2-oxo-2,3-dihydro-benzooxazoly, R$_g$ is optionally substituted with one to three R$_h$ groups selected from halogen, hydroxyl, C$_{1-6}$alkyl, benzyl, C$_{1-6}$alkoxy, phenoxy, phenylamino, hydroxyC$_{1-6}$alkyl, —CN, —CO$_2$H, —CO$_2$C$_{1-6}$alkyl, —N(R$_c$)(R$_d$), C$_{1-6}$alkylN(R$_c$)(R$_d$), —C(O)N(R$_c$)(R$_d$), —NO$_2$, —C(O)$_n$C$_{1-6}$alkyl and —S(O)$_n$N(R$_c$)(R$_d$), or R$_h$ is an aryl or a heteroaryl group selected from phenyl, imidazolyl, pyrazolyl, thienyl, oxazoly, thiazolyl, pyridyl, pyrimidyl, pyrazinyl, benzo[1,3]dioxoly, and quinolinyl, or R$_h$ is morpholinyl, R$_h$ is optionally substituted with one to three R$_i$ groups selected from halogen, hydroxyl, C$_{1-6}$alkyl, C$_{1-6}$alkoxy, —CN, —CO$_2$H, —CO$_2$C$_{1-6}$alkyl, —N(R$_c$)(R$_d$) and C(O)N(R$_c$)(R$_d$);

m is 0 or 1;

n is 0, 1 or 2; and p is 0, 1, 2 or 3;

or the pharmaceutically acceptable salts, esters, isomers or tautomers thereof.

An eighth embodiment of the invention comprises a compound of formula (III) as described in the seventh embodiment wherein:

R$_1$ is (a) phenyl or heteroaryl selected from furanyl, thienyl, pyridyl, pyrrolyl, imidazolyl and benzofuranyl, optionally substituted with one to two R$_a$, (b) heterocyclyl selected from 1-piperidinyl, 1-piperazinyl, 1-pyrrolidinyl and 4-morpholinyl, optionally substituted with one to two groups selected from C$_{1-6}$alkyl, —CO$_2$C$_{1-5}$alkyl, phenyl, benzyl, —OH and —C(O)heteroaryl, wherein the heteroaryl is selected from furanyl, thienyl, pyridyl and pyrrolyl, (c) R$_b$(CH$_2$)$_m$O—, (d) C$_{3-6}$-cycloalkyl, (e) C$_{3-6}$-cycloalkylC$_{1-3}$alkyl (f) R$_b$OCH$_2$—, (g) R$_b$(CH$_2$)$_m$NH—, (h) R$_b$(CH$_2$)$_p$(CH=CH)$_m$—, (i) C$_{1-6}$alkyl, (j) C$_{1-8}$alkoxy, (k) C$_{1-8}$alkylthio, (l) C$_{1-6}$alkoxyC$_{1-6}$alkoxy, (m) —CF$_3$, (n) —CHO, (o) —OCH$_2$CO$_2$H, (p) —OSO$_2$CF$_3$, (q) —N(R$_c$)(R$_d$), or (r) —C(O)NR$_c$R$_d$;

R$_2$ is (a) C$_{1-6}$alkyl-OC(O)C$_{1-6}$alkoxy, (b) hydroxyC$_{1-6}$alkyl-, (c) hydroxyC$_{1-6}$alkoxy-, optionally substituted with —C(O)C$_{1-6}$alkyl, (d) (R$_c$)(R$_d$)NC$_{1-6}$alkoxy-, (e) (R$_c$)(R$_d$)NC$_{1-6}$alkyl-, (f) hydroxyC$_{1-6}$alkylamino-, (g) (R$_c$)(R$_d$)NC$_{1-6}$alkylamino-, (h) C$_{1-6}$alkoxyC$_{1-6}$alkylamino-, (i) heterocyclyl(CH$_2$)$_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two R$_e$, (j) heterocyclylCH$_2$O— wherein the heterocyclyl is selected from 1-piperidinyl, 1-piperazinyl, 4-morpholinyl and 1-pyrrolidinyl, optionally substituted with C$_{1-6}$alkyl, (k) R$_b$(CH$_2$)$_m$O—, (l) heteroaryl(CH$_2$)$_m$O—, wherein the heteroaryl is selected from furanyl, thienyl, imidazolyl, pyridyl, indolyl and pyrrolyl, (m) heteroarylC$_{1-6}$alkylamino, wherein the heteroaryl is selected from furanyl, thienyl, imidazolyl, pyridyl, indolyl and pyrrolyl, (n) —SC$_{1-6}$alkyl, or (o) —SC$_{1-6}$alkylC(O)N(R$_4$)(R$_5$);

R$_3$ is —N(R$_c$)(R$_d$);

R$_a$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N(R$_c$)(R$_d$), —NHC(O)NHC$_{1-6}$alkyl, —C(O)N(R$_c$)(R$_d$) and phenyl optionally substituted with halogen, C$_{1-6}$alkyl, —CN or C$_{1-6}$alkoxy;

R$_b$ is a phenyl group optionally substituted with one or two groups selected from halogen, 1-naphthyl, C$_{1-6}$alkyl, —CN, —CO$_2$C$_{1-6}$alkyl, —C(O)N(R$_c$)(R$_d$), NO$_2$ and C$_{1-6}$alkoxy, or R$_b$ is C$_{3-6}$cycloalkyl;

R$_c$ and R$_d$ are independently selected from H, C$_{1-6}$alkyl, —C(O)C$_{1-4}$alkyl, —SO$_2$C$_{1-6}$alkyl, phenyl, benzyl, piperidinyl, phenylethyl and (CH$_3$)$_3$COC(O)—;

R$_e$ is selected from —OH, —NH$_2$, —NHCHO, —O(CH$_2$)phenyl, amino, —CN, oxo, —CO$_2$C$_{1-6}$alkyl, —CO$_2$H, —C(O)N(R$_c$)(R$_d$), —N(R$_c$)(R$_d$), —CH$_2$N(R$_c$)(R$_d$), —CH$_2$OH, C$_{1-6}$alkyl, —CO$_2$benzyl, hydroxyC$_{1-6}$alkyl, —C(O)C$_{1-6}$alkylN(R$_c$)(R$_d$), —NHCO$_2$C$_{1-6}$alkyl, HOCH(R$_b$)CH$_2$NH—, —NHC(O)N(R$_c$)(R$_d$), —S(O)$_n$C$_{1-6}$alkyl, (CH$_3$)$_3$COC(O)—, phenyl, pyridyl, H$_2$NCH(R$_f$)C(O)— and —C(O)heterocyclyl, wherein said heterocyclyl is selected from piperidinyl, piperazinyl, morpholinyl and pyrrolidinyl;

R$_f$ is selected from C$_{1-6}$alkyl, —(CH$_2$)$_{1-4}$NH$_2$, phenyl or benzyl;

m is 0 or 1;

n is 0, 1 or 2; and p is 0, 1, 2 or 3;

or the pharmaceutically acceptable salts, esters, isomers or tautomers thereof.

An ninth embodiment of the invention comprises a compound of formula (III) as described in the eighth embodiment wherein:

R$_1$ is (a) C$_{1-6}$alkyl, (b) C$_{1-4}$alkoxy, (c) C$_{3-6}$-cycloalkyl, (d) C$_{3-6}$-cycloalkylC$_{1-3}$alkyl (e) C$_{1-4}$alkylthio, (f) —CF$_3$, or (g) —C(O)NR$_c$R$_d$;

R₂ is
heterocyclyl wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$;

$R_3$ is —NH₂; and $R_c$ and $R_d$ are independently selected from H, $C_{1-6}$alkyl, —C(O)$C_{1-6}$alkyl, —SO₂$C_{1-6}$alkyl, phenyl, benzyl, piperidinyl, phenylethyl and (CH₃)₃COC(O)—;

$R_e$ is selected from —OH, —NH₂, —NHCHO, —O(CH₂)phenyl, amino, —CN, oxo, —CO₂$C_{1-6}$alkyl, —CO₂H, —C(O)N($R_c$)($R_d$), —N($R_c$)($R_d$), —CH₂N($R_c$)($R_d$), —CH₂OH, $C_{1-6}$alkyl, —CO₂benzyl, hydroxy$C_{1-6}$alkyl, —C(O)$C_{1-6}$alkylN($R_c$)($R_d$), —NHCO₂$C_{1-6}$alkyl, HOCH($R_b$)CH₂NH—, —NHC(O)N($R_c$)($R_d$), —S(O)$_n$$C_{1-6}$alkyl, (CH₃)₃COC(O)—, phenyl, pyridyl, H₂NCH($R_f$)C(O)— and —C(O)heterocyclyl, wherein said heterocyclyl is selected from piperidinyl, piperazinyl, morpholinyl and pyrrolidinyl;

$R_f$ is selected from $C_{1-6}$alkyl, —(CH₂)$_{1-4}$NH₂, phenyl or benzyl;

m is 0 or 1;

n is 0, 1 or 2; and p is 0, 1, 2 or 3;

or the pharmaceutically acceptable salts, esters, isomers or tautomers thereof.

In a tenth embodiment of the invention there are provided the following compounds listed in Table 1:

TABLE 1

| Compound No. | Name | Structure | LCMS with ES source M + 1 found |
|---|---|---|---|
| 1. | 7-(4-Methyl-[1,4]diazepan-1-yl)-9-propyl-pyrido[3',2':4,5]thieno[3,2-d]pyrimidin-4-ylamine | 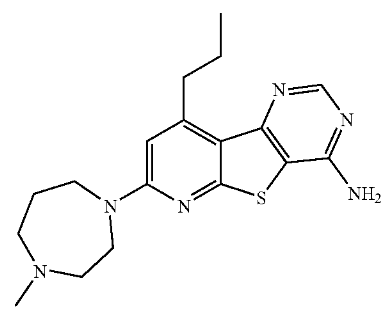 | 357 |
| 2. | 7-(4-Benzyloxy-piperidin-1-yl)-9-propyl-pyrido[3',2':4,5]thieno[3,2-d]pyrimidin-4-ylamine | 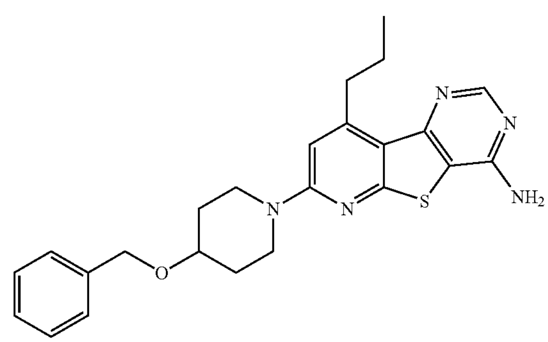 | 434 |
| 3. | N-[1-(4-Amino-9-propyl-pyrido[3',2':4,5]thieno[3,2-d]pyrimidin-7-yl)-piperidin-4-yl]-formamide | 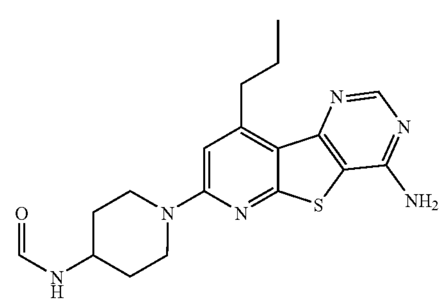 | 371 |

TABLE 1-continued

| Compound No. | Name | Structure | LCMS with ES source M + 1 found |
|---|---|---|---|
| 4. | [1-(4-Amino-9-propyl-pyrido[3',2':4,5]thieno[3,2-d]pyrimidin-7-yl)-piperidin-4-yl]-carbamic acid benzyl ester | 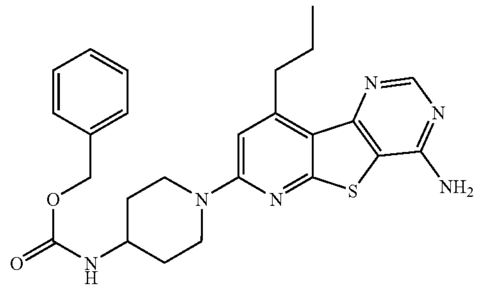 | 477 |
| 5. | 1-(4-Amino-9-propyl-pyrido[3',2':4,5]thieno[3,2-d]pyrimidin-7-yl)-piperidin-4-ol | 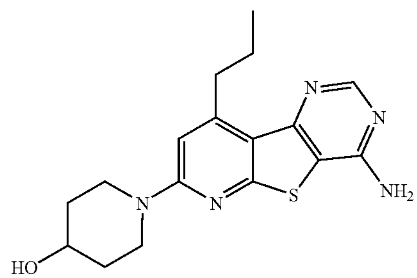 | 344 |
| 6. | N-[1-(4-Amino-9-propyl-pyrido[3',2':4,5]thieno[3,2-d]pyrimidin-7-yl)-piperidin-4-yl]-methanesulfonamide | 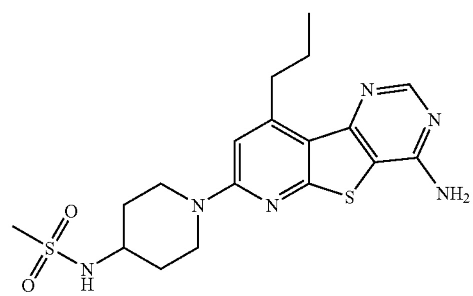 | 421 |
| 7. | 7-(4-Amino-piperidin-1-yl)-9-propyl-pyrido[3',2':4,5]thieno[3,2-d]pyrimidin-4-ylamine | 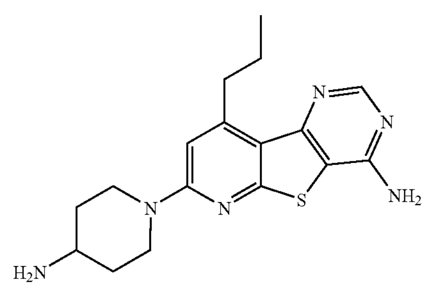 | 343 |
| 8. | 1-(4-Amino-9-propyl-pyrido[3',2':4,5]thieno[3,2-d]pyrimidin-7-yl)-piperidin-4-one | 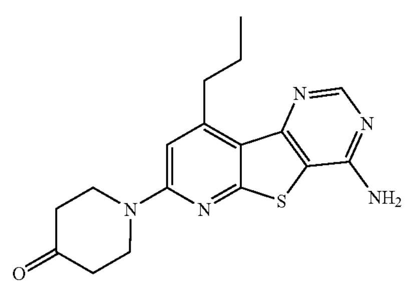 | 342 |

TABLE 1-continued

| Compound No. | Name | Structure | LCMS with ES source M + 1 found |
|---|---|---|---|
| 9. | 2-[1-(4-Amino-9-propyl-pyrido[3',2':4,5]thieno[3,2-d]pyrimidin-7-yl)-piperidin-4-ylamino]-1-naphthalen-1-yl-ethanol | 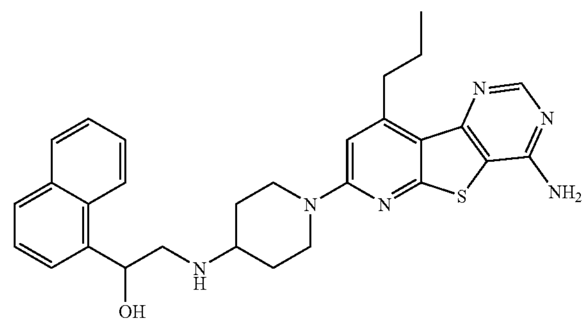 | 513 |
| 10. | (S)-2-[1-(4-Amino-9-propyl-pyrido[3',2':4,5]thieno[3,2-d]pyrimidin-7-yl)-piperidin-4-ylamino]-1-phenyl-ethanol | 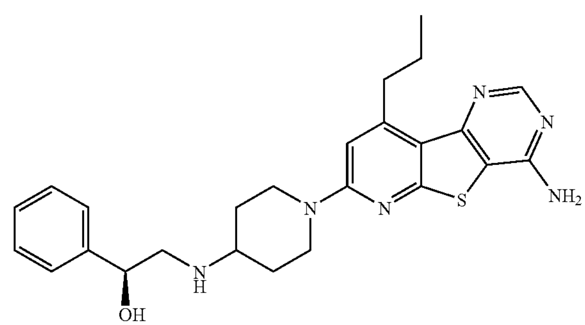 | 463 |
| 11. | 4-{2-[1-(4-Amino-9-propyl-pyrido[3',2':4,5]thieno[3,2-d]pyrimidin-7-yl)-piperidin-4-ylamino]-1-hydroxy-ethyl}-benzamide | 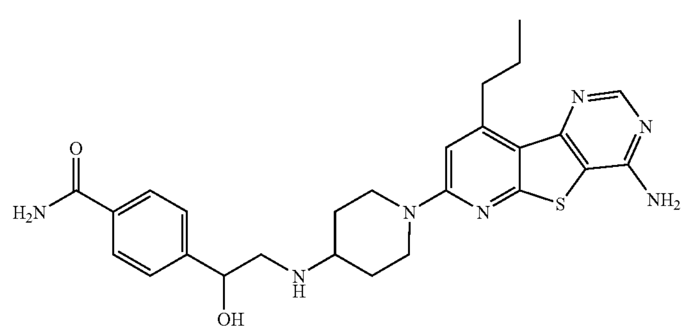 | 506 |
| 12. | 7-(4-Amino-piperidin-1-yl)-9-trifluoromethyl-pyrido[3',2':4,5]thieno[3,2-d]pyrimidin-4-ylamine | 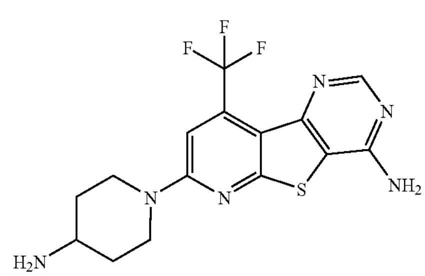 | 369 |

TABLE 1-continued

| Compound No. | Name | Structure | LCMS with ES source M + 1 found |
|---|---|---|---|
| 13. | N-[1-(4-Amino-9-trifluoromethyl-pyrido[3',2':4,5]thieno[3,2-d]pyrimidin-7-yl)-piperidin-4-yl]-formamide | 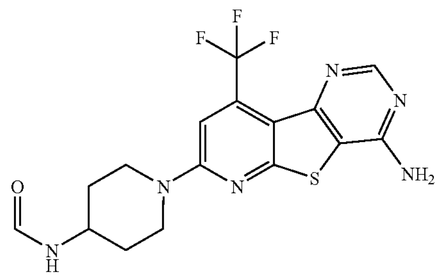 | 397 |
| 14. | 1-(2,4-Diamino-9-propyl-pyrido[3',2':4,5]thieno[3,2-d]pyrimidin-7-yl)-piperidin-4-ol | 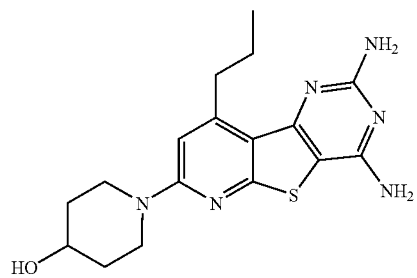 | 359 |
| 15. | 1-(4-Amino-9-propyl-pyrido[3',2':4,5]thieno[3,2-d][1,2,3]triazin-7-yl)-piperidin-4-ol | 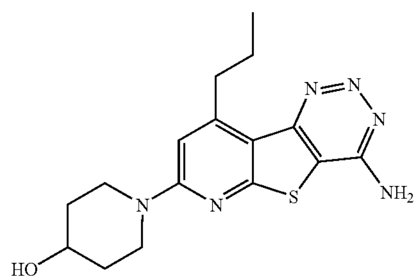 | 345 |
| 16. | 1-(8-Amino-4-propyl-9-thia-1,7-diaza-fluoren-2-yl)-piperidin-4-one | 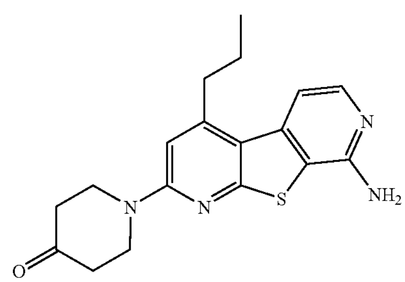 | 341 |
| 17. | (S)-2-[1-(8-Amino-4-propyl-9-thia-1,7-diaza-fluoren-2-yl)-piperidin-4-ylamino]-1-phenyl-ethanol | | 462 | or the pharmaceutically acceptable salts, esters, isomers or tautomers thereof.

In an eleventh embodiment of the invention there are provided compounds:

N-[1-(4-Amino-9-propyl-pyrido[3',2':4,5]thieno[3,2-d]pyrimidin-7-yl)-piperidin-4-yl]-methanesulfonamide 7-(4-Amino-piperidin-1-yl)-9-propyl-pyrido[3',2':4,5]thieno[3,2-d]pyrimidin-4-ylamine 1-(4-Amino-9-propyl-pyrido[3',2':4,5]thieno[3,2-d]pyrimidin-7-yl)-piperidin-4-one 2-[1-(4-Amino-9-propyl-pyrido[3',2':4,5]thieno[3,2-d]pyrimidin-7-yl)-piperidin-4-ylamino]-1-naphthalen-1-yl-ethanol (S)-2-[1-(4-Amino-9-propyl-pyrido[3',2':4,5]thieno[3,2-d]pyrimidin-7-yl)-piperidin-4-ylamino]-1-phenyl-ethanol 4-{2-[1-(4-Amino-9-propyl-pyrido[3',2':4,5]thieno[3,2-d]pyrimidin-7-yl)-piperidine-4-ylamino]-1-hydroxy-ethyl}-benzamide 7-(4-Amino-piperidin-1-yl)-9-trifluoromethyl-pyrido[3',2':4,5]thieno[3,2-d]pyrimidin-4-ylamine N-[1-(4-Amino-9-trifluoromethyl-pyrido[3',2':4,5]thieno[3,2-d]pyrimidin-7-yl)-piperidin-4-yl]-formamide;

or the pharmaceutically acceptable salts, esters, isomers or tautomers thereof.

In all the compounds disclosed hereinabove, in the event the nomenclature is in conflict with the structure, it shall be understood that the compound is defined by the structure.

The invention includes pharmaceutically acceptable derivatives of compounds of formula (I). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N-($C_1$-$C_4$ alkyl)$_4^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:
DMF is dimethylformamide;
DMSO is dimethyl sulfoxide
EtOAc is ethyl acetate;
EtOH is ethanol;
HPLC is high-performance liquid chromatography
MeOH is methanol;
THF is tetrahydrofuran;
TLC is thin layer chromatography Terms not specifically defined herein should be given the meanings that would be given to them by one of skill in the art in light of the disclosure and the context. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched, unbranched unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms.

The term "heterocycloalkyl" refers to a stable 4-8 membered (but preferably, 5 or 6 membered) monocyclic or 8-11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycloalkyl" include radicals such as pyrrolinyl, pyrrolidinyl, pyrazolinyl, pyrazolidinyl, piperidinyl, morpholinyl, thiomorpholinyl, piperazinyl, indolinyl, azetidinyl, tetrahydropyranyl, tetrahydrothiopyranyl, tetrahydrofuranyl, hexahydropyrimidinyl, hexahydropyridazinyl, dihydro-oxazolyl, 1,2-thiazinanyl-1,1-dioxide, 1,2,6-thiadiazinanyl-1,1-dioxide, isothiazolidinyl-1,1-dioxide and imidazolidinyl -2,4-dione.

The term "halogen" refers to bromine, chlorine, fluorine or iodine.

The term "aryl" shall be understood to mean a 6-12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "heteroaryl" refers to a stable 5-8 membered (but preferably, 5 or 6 membered) monocyclic or 8-11 membered bicyclic aromatic heterocycle radical. Each heterocycle consists of carbon atoms and from 1 to 4 heteroatoms chosen from nitrogen, oxygen and sulfur. The heteroaryl group may be attached by any atom of the ring which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

As used herein above and throughout this application, "nitrogen" and "sulfur" include any oxidized form of nitrogen and sulfur and the quaternized form of any basic nitrogen.

Methods of Therapeutic Use

In accordance with the invention, there are provided novel methods of using the compounds of the formula (I). The compounds of the invention are effective in inhibiting the activity of IKKβ and/or IKKα. In particular, these compounds are useful in blocking disease processes exacerbated by IKKβ-mediated NF-κB activation and IKKα activation of B cell activity or the cell cycle regulatory gene Cyclin D1. In blocking NF-κB activation, compounds of the invention effectively block transcription of genes encoding inflammatory cytokines including IL-1, IL-2, IL-6, IL-8, TNFα, chemokines including IL-8 and RANTES as well as other pro-inflammatory molecules including COX-2 and cell adhesion molecules such as ICAM-1, VCAM-1 and E-selectin. These mediators play a key role in the etiology of inflammatory and autoimmune disorders. Preventing the production of these mediators is a desirable means for treating these disorders. Thus there are provided methods for treating these conditions using the compounds of the invention. Such inflammatory and autoimmune conditions include but are not limited to osteoarthritis, reperfusion injury, asthma, multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain as well as symptoms of inflammation and cardiovascular disease, stroke, myocardial infarction alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. The compounds of the invention can also be used to treat other disorders associated with IKK activation of NF-κB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

By inhibiting the kinase activity of IKKα, compounds of the invention are useful in treating inflammatory conditions where B cells contribute to the etiology of the disease, including but not limited to lupus and rheumatoid arthritis. They are also useful for the treatment of breast cancer by inhibiting the induction of Cyclin D1. The compounds of the invention can also be used to treat other disorders associated with inappropriate IKKα activity, unrelated to those listed above or discussed in the Background of the Invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

General Synthetic Methods

The invention additionally provides methods for making the compounds of formulas I, II and III. The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization.

Compounds of the invention of formula I having $R_4$=H may be made by Method A or Method B as illustrated in Scheme I below.

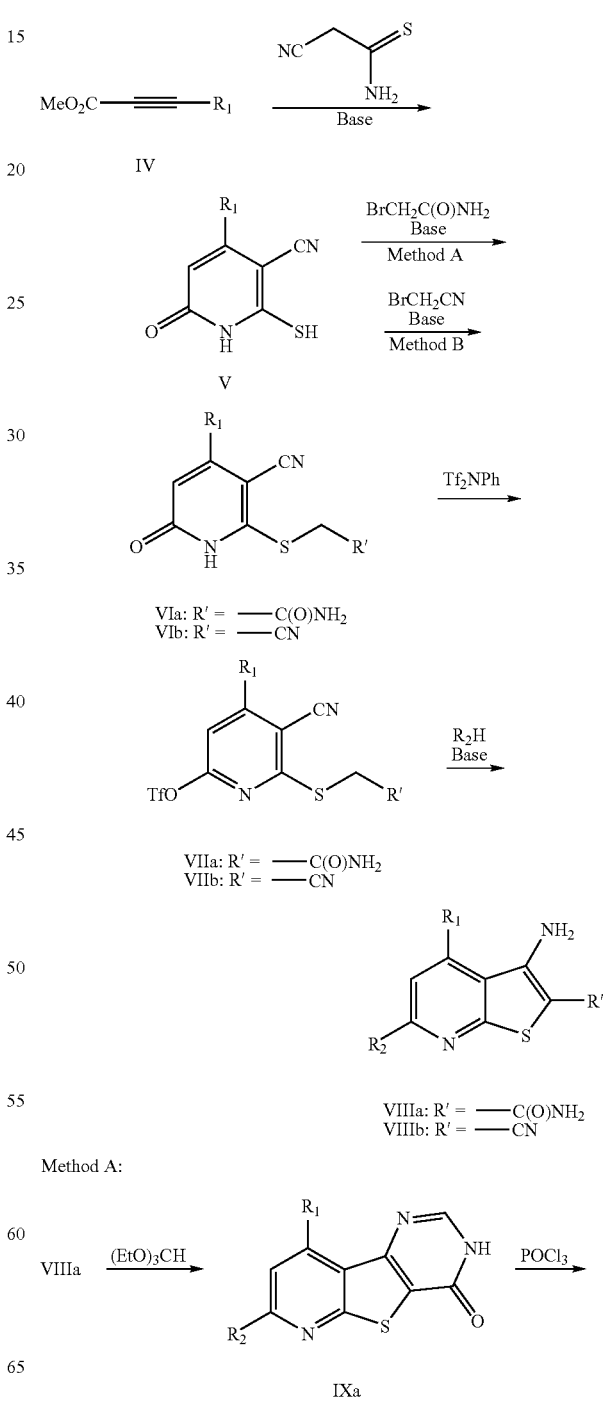

-continued

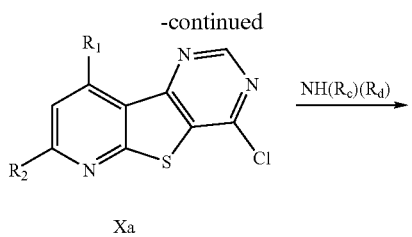
Xa

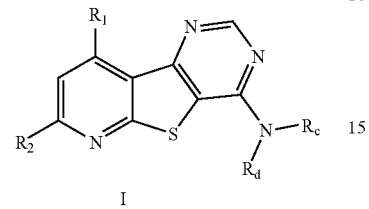
I

Method B:

VIIIb $\xrightarrow{HC(O)NH_2}$

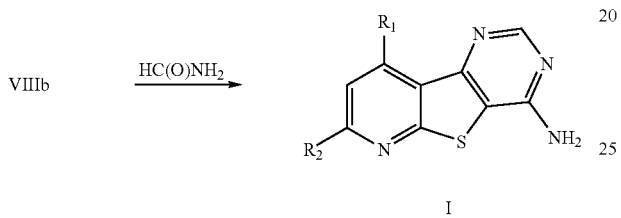
I

An alkynoate ester bearing $R_1$, such as the methyl ester IV shown above, is reacted with 2-cyanothioacetamide in the presence of a suitable base such as morpholine to provide the mercaptopyridine V. Intermediate V may then be reacted with 2-bromoacetamide in the presence of a suitable base such as potassium carbonate to produce mercaptoacetamide VIa (Method A). Alternately, V may be reacted with 2-bromoacetonitrile using conditions described in Method A to provide the mercaptoacetonitrile VIb (Method B).

Proceeding with Method A, one reacts VIa with a trifluoromethylsulfonylating reagent such as N-phenyltrifluoromethanesulfonimide in the presence of a suitable base such as triethylamine to form the trifluoromethanesulfonic acid ester VIIa. Reaction of VIIa with a nucleophilic $R_2H$ such as an amine, alcohol or thiol in the presence of a suitable base provides amide VIIIa with an amine, ether or thioether at $R_2$ respectively. The same sequence with VIb provides the nitrile VIIIb (Method B).

Using Method A, VIIIa is heated with triethylorthoformate in a suitable solvent such as EtOH, in the presence of a catalytic amount of an acid such as glacial acetic acid to provide the pyridothienopyrimidinone IXa. Reaction of IXa with a suitable chlorinating reagent such as phosphorous oxychloride provides the chloro intermediate Xa. Reaction of Xa with the desired amine —NH($R_c$)($R_d$), preferably while heating in a sealed vessel, provides the desired compound of formula I ($R_3$=—NH($R_c$)($R_d$), $R_4$=H).

Using Method B, one reacts the nitrile VIIb with formamide, preferably by heating in a microwave-assisted reactor, to provide the desired compound of formula I ($R_2$=an amine, ether or thioether, $R_3$=$NH_2$, $R_4$=H). Initially formed $R_1$ and $R_2$ groups of VIIIa, VIIIb or I may be further reacted by methods known in the art to provide additional compounds of formula I.

Compounds of formula I having $R_3$=$R_4$=$NH_2$ may be prepared as illustrated in Scheme II. Heating VIIIb with a guanidine salt such as guanidine carbonate provides I ($R_3$=$R_4$=$NH_2$).

Scheme II

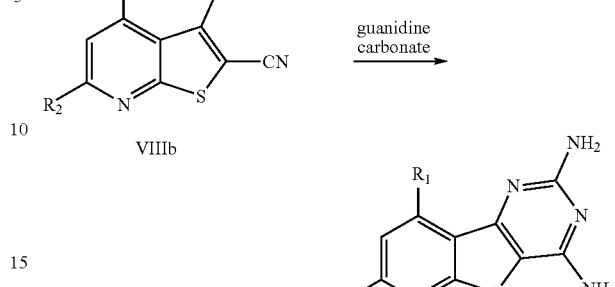

Compounds of formula II may be prepared as described in Scheme III. Reaction of VIIIb with isoamyl nitrite and HCl in a suitable solvent such as EtOH provides XI. Reaction of XI with ammonia, preferably while heating in a sealed tube provides II ($R_3$=$NH_2$).

Scheme III

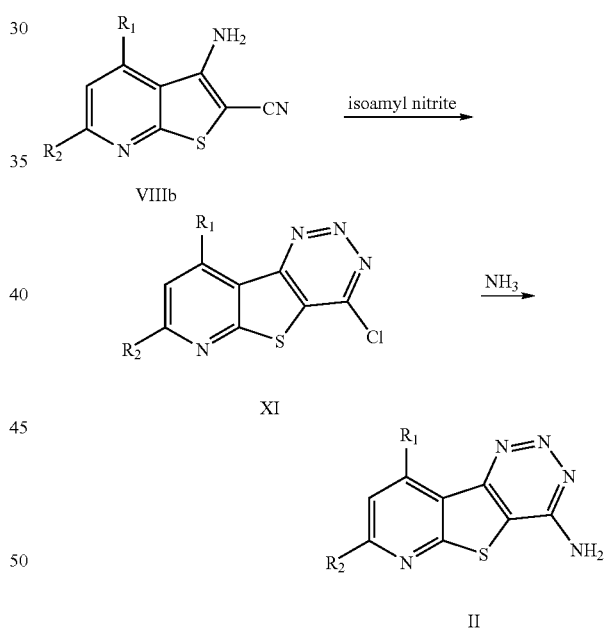

Compounds of formula III may be prepared as illustrated in Scheme IV.

Scheme IV

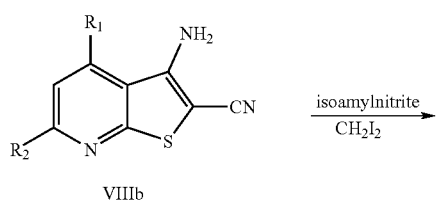
VIIIb

SYNTHETIC EXAMPLES

Example 1

Synthesis of 7-(4-methyl-[1,4]diazepan-1-yl)-9-propyl-pyrido[3',2':4,5]thieno[3,2-d]pyrimidin-4-ylamine Method A:

As illustrated above, diazotization of the amino group of VIIIb, for example by treatment with isoamylnitrite, followed by reaction with an iodine source such as $CH_2I_2$ provides the iodo intermediate XII. A cross coupling reaction of XII with trimethylsilylacetylene provides XIII. Removal of the trimethylsilyl group, for example by treatment with tetrabutylammonium fluoride, provides the acetylene intermediate XIV. Treatment of XIV with an ammonia source such as ammonium hydroxide, in a suitable solvent such as dioxane while heating in a sealed reaction vessel provides the desired product of formula III.

Compounds of the invention having other $R_1$ and $R_2$ described in the Detailed Description of the Invention may be prepared by methods known in the art. For example U.S. Application No. 60/386,312, incorporated herein by reference, describes several syntheses of VIIIa with a variety of different $R_1$ and $R_2$. These intermediates may then be reacted further by Method A to prepare additional compounds of formula I. Intermediates of formula VIIIa may be converted to the nitrile VIIb by methods known in the art for example by treatment with a dehydrating agent such as phosphorous pentoxide, phosphorous oxychloride or cyanuric chloride. The resulting VIIIb may then be reacted further as described in Method B, Scheme II or Scheme III to provide additional compounds of the invention.

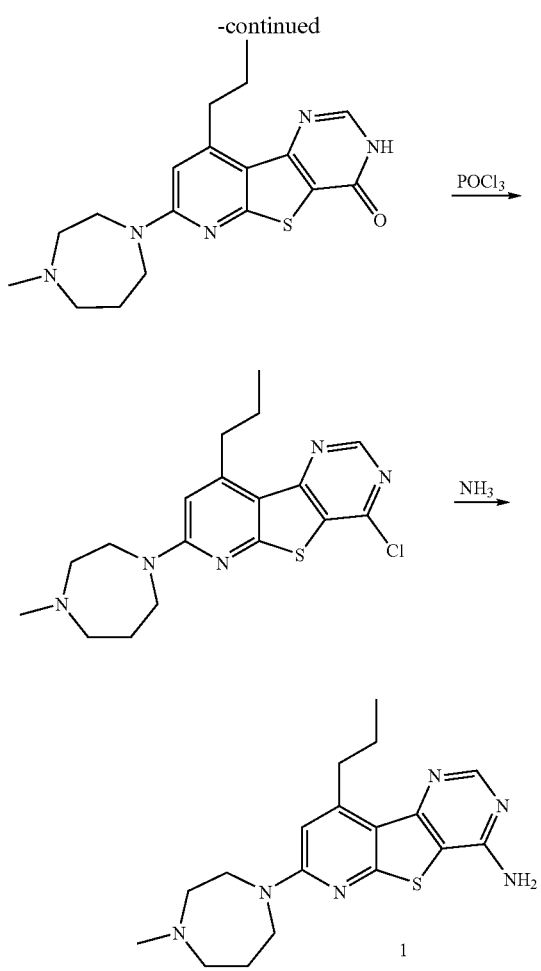

To a solution of methyl 2-hexanoate (15 g, 0.119 mol) in EtOH (40 mL) was added morpholine (10.5 g, 0.120 mol) dropwise at room temperature. The solution was then warmed to 45° C. for 4 h under nitrogen. Solid NCCH$_2$C(S)NH$_2$ (12.1 g, 0.120 mol) was then added in small portions. After stirring at 45° C. for 30 min, the mixture was stirred at room temperature overnight. The yellow precipitate was collected by filtration, giving 10.9 g of the desired mercaptopyridone as a complex with 1 molecule of morpholine.

A mixture of the above mercaptopyridone (5.25 g, 18.68 mmol), 2-bromoacetamide (2.58 g, 18.68 mmol) and K$_2$CO$_3$ (2.58 g, 18.68 mmol) in dry DMF (50 mL) was heated under Ar at 70° C. for 4 h. The mixture was then cooled to 0° C., and acidified to pH~2 with 6 N HCl (~3 mL). The mixture was kept at 0° C. for 2 h, and the resulting white precipitate was collected by filtration. The product was washed with cold water to give 5.5 g of the desired mercaptoacetamide.

To a mixture of the above mercaptoacetamide (4.15 g, 16.54 mmol)) and iPr$_2$NEt (4.6 mL, 32.82 mmol) in dry dioxane (40 mL) was added N-phenyltrfluoromethane-sulfonimide (5.91 g, 16.54 mmol) in small portions. The mixture was stirred under nitrogen for 16 h, concentrated and purified by silica gel column chromatography eluting with 50-80% EtOAc-hexane (gradient) to give 4.7 g of the desired 2-(3-cyano-4-n-propyl-6-trifluoromethanesulfonylpyridin-2-ylmercapto)acetamide.

To a stirred solution of the above triflate (0.200 g, 2.08 mmol) in 1,4-dioxane was added 1-methylhomopiperazine (0.32 mL, 2.5 mmol) followed by triethylamine (1.0 mL, 7.4 mmol) at room temperature, under nitrogen (a white precipitate forms). The resulting suspension was warmed to 80° C. for 1 h and cooled to ambient temperature (reaction complete by TLC, SiO$_2$, 10% MeOH/CH$_2$Cl$_2$). The reaction was treated with 2 M Na$_2$CO$_3$ (2 mL) and warmed to 100° C. for 3 h and then at 70° C. for 48 h (reaction complete by TLC, SiO$_2$, 0.5% NH$_4$OH/10% MeOH/CH$_2$Cl$_2$). After cooling to room temperature, the reaction was diluted with EtOAc and the layers were separated. The aqueous phase was extracted with EtOAc (2×). The combined organics were treated with SiO$_2$ (~0.8 g) and the resulting suspension was concentrated. The resulting solid was purified by flash chromatography (35 g SiO$_2$, 0.5% NH$_4$OH/6% MeOH/CH$_2$Cl$_2$, flow rate 30 mL/min, UV detection at 254 nm). 3-Amino-6-(4-methyl-[1,4]diazepan-1-yl)-4-propyl-thieno[2,3-b]pyridine-2-carboxylic acid amide (0.590 g) was isolated as an off-white solid.

To a stirred suspension of the above amide (0.590 g, 1.70 mmol) in EtOH and triethyl orthoformate (5.0 mL) was added glacial acetic acid (5 drops). The resulting mixture was warmed to 90° C. (became homogenous) over the weekend during which time a precipitate formed. The reaction was cooled to room temperature and the solid was collected via filtration and washed with EtOH to give 0.450 g of 7-(4-methyl-[1,4]diazepan-1-yl)-9-propyl-3H-pyrido[3',2':4,5]thieno[3,2-d]pyrimidin-4-one as a white solid.

A suspension of the above pyrimidin-4-one (0.270 g, 0.755 mmol) in phosphorous oxychloride (0.7 mL) was warmed to 95° C. under nitrogen (became a homogenous/red-orange solution). After 0.5 h, a solid formed and the reaction was cooled to ambient temperature. The excess phosphorous oxychloride was removed under high vacuum. The resulting tan solid was washed twice with hexane and dried under high vacuum providing 0.300 g of 4-chloro-7-(4-methyl-[1,4]diazepan-1-yl)-9-propyl-pyrido[3',2':4,5]thieno[3,2-d]pyrimidine.

In a Parr steel vessel at −78° C., the above chloropyrimidine (150 mg, 0.334 mmol) was suspended in 3 mL of dioxane and 5 mL of liquid ammonia. This mixture was then heated in the Parr pressure vessel at 100° C. for 20 h. The vessel was then cooled to −78° C. and opened and allowed to warm up to room temperature slowly. The resulting suspension was diluted with water and the suspended solid was collected by filtration and washed with water then air dried. The crude product was recrystallized from MeOH and ether to provide the title compound (30 mg, 86%).

Method B:

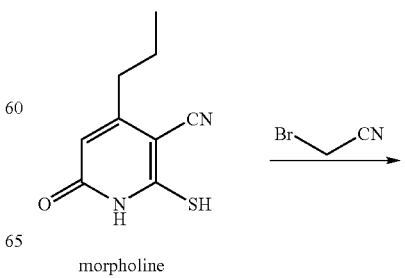

morpholine

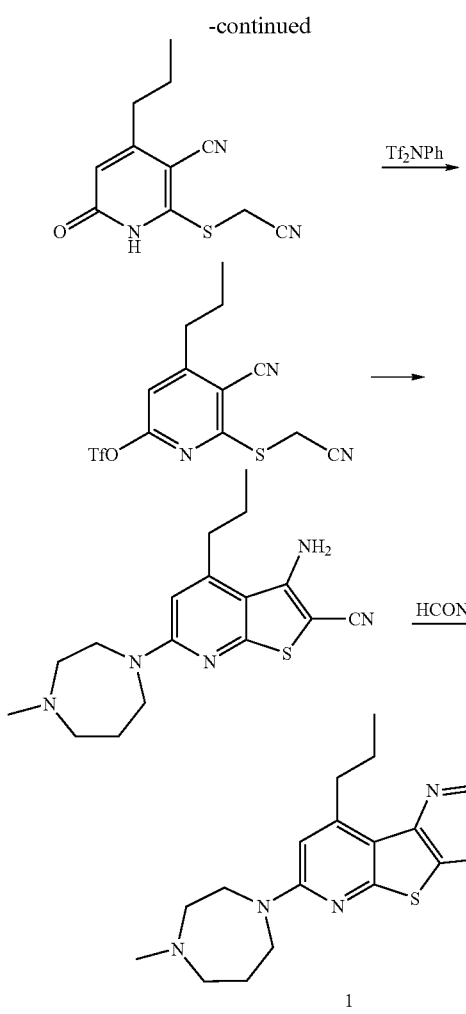

The morpholine salt of 2-mercapto-6-oxo-4-propyl-1,6-dihydro-pyridine-3-carbonitrile (see above) was reacted with 2-bromoacetonitrile as described above for 2-bromoacetamide to provide 2-cyanomethylsulfanyl-6-oxo-4-propyl-1,6-dihydro-pyridine-3-carbonitrile. This nitrile (19.02 g, 81.53 mmol) and N-phenyltrifluoromethanesulfonimide (29.59 g, 82.00 mmol) were dissolved in 100 mL of dry dioxane. Diisopropylethylamine (19.3 mL, 135 mmol) was added and the mixture was stirred at room temperature under argon for 4 h. The solvent was concentrated. The residue was dissolved in EtOAc and ether and the resulting solution was filtered through a pad of silica gel which was washed with ether. The filtrate was concentrated and the resulting yellow solid was collected by filtration and dried under vacuum to provide trifluoro-methanesulfonic acid 5-cyano-6-cyanomethylsulfanyl-4-propyl-pyridin-2-yl ester (18.45 g, 62%).

The above ester (0.548 g, 1.50 mmol), 1-methylhomopiperizine (0.19 mL, 1.5 mmol) and triethylamine (0.21 mL, 1.5 mmol) were dissolved in 2 mL of dioxane. The reaction mixture was heated in a SmithSynthesizer™ (Personal Chemistry) at 100° C. for 2 h. After cooling to room temperature, the reaction mixture was poured into water and the suspended solid was filtered and dried under vacuum to give 3-amino-6-(4-methyl-[1,4]diazepan-1-yl)-4-propyl-thieno[2,3-b]pyridine-2-carbonitrile as a light green solid, (336 mg, 68%).

The above nitrile (316 mg, 1.00 mmol) and formamide (3 mL) were heated in a SmithSynthesizer™ (Personal Chemistry) at 150° C. for 16 h. The reaction mixture was poured into water and the resulting solid was collected by filtration. The solid was further purified by flash chromatography (35 g silica gel cartridge, 10 mL hexane/EtOAc 20-0% in 30 min, 0% for 30 min, 0.1% ammonium hydroxide) to give the title compound as yellow solid (198 mg, 56%).

Example 2

Synthesis of 1-(4-amino-9-propyl-pyrido[3',2':4,5]thieno[3,2-d]pyrimidin-7-yl)-piperidin-4-ol

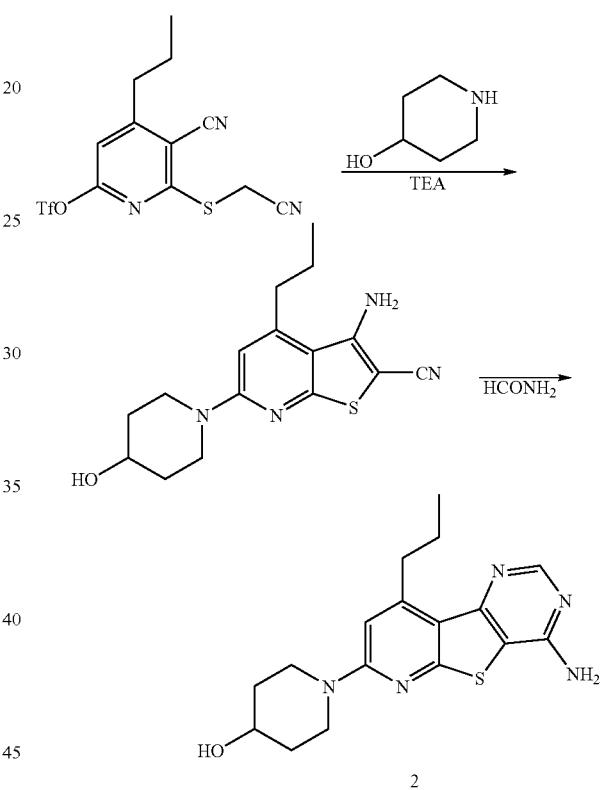

Trifluoro-methanesulfonic acid 5-cyano-6-cyanomethylsulfanyl-4-propyl-pyridin-2-yl ester (1.10 g, 3.00 mmol) (see Example 1, Method B) and 4-hydroxypiperidine (310 mg, 3.00 mmol) was suspended in 2 mL of dioxane. Triethylamine (0.84 mL, 6.0 mmol) was added and the reaction mixture was heated in a SmithSynthesizer™ (Personal Chemistry) at 100° C. for 2 h. This reaction mixture was poured into water and the resulting solid was collected by filtration and air dried to provide 3-amino-6-(4-hydroxy-piperidin-1-yl)-4-propyl-thieno[2,3-b]pyridine-2-carbonitrile (845 mg, 89%).

The above nitrile (316 mg, 1.0 mmol) and formamide (3 μL) were heated in a SmithSynthesizer™ (Personal Chemistry) at 150° C. for 16 h. The reaction mixture was poured into water and the resulting solid was collected by filtration. The solid was further purified with HPLC (Shimadzu, Thermohypersil PEP 100-C18, 254 nM, acetonitrile/water 15-70% in 25 minutes, retention time=12.61 min) to give the title compound as a white solid (120 mg, 35%).

Example 3

Synthesis of 7-(4-amino-piperidin-1-yl)-9-propyl-pyrido[3',2':4,5]thieno[3,2-d]pyrimidin-4-ylamine

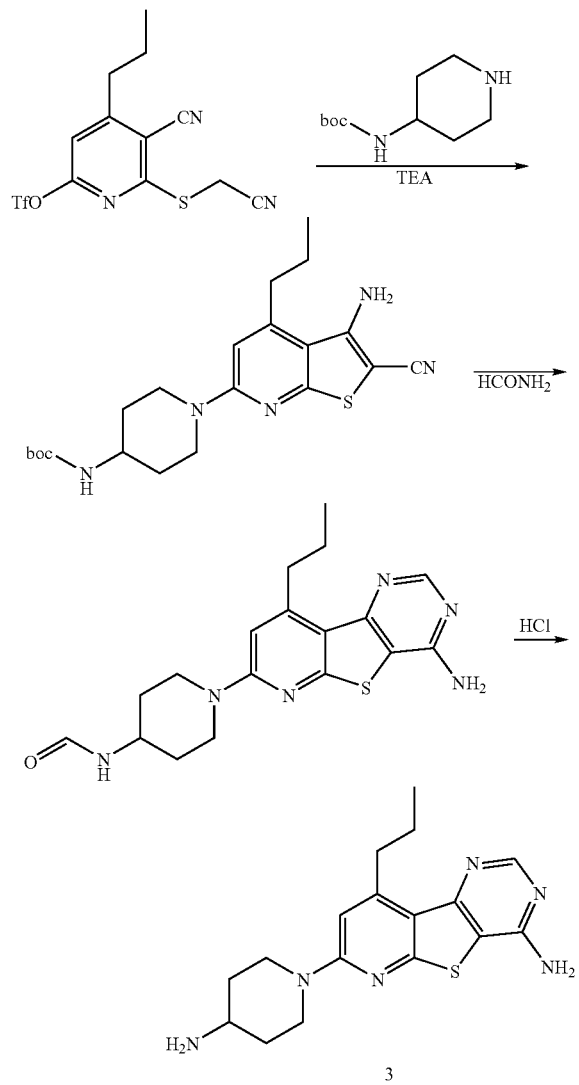

Trifluoro-methanesulfonic acid 5-cyano-6-cyanomethyl-sulfanyl-4-propyl-pyridin-2-yl ester (1.10 g, 3.00 mmol) (see Example 1, Method B) and 4-N-boc-amino-piperidine (613 mg, 3.00 mmol) was suspended in 2 mL of dioxane. Triethylamine (0.84 mL, 6.0 mmol) was added. The reaction mixture was heated in a SmithSynthesizer™ (Personal Chemistry) at 100° C. for 2 h. The reaction mixture was poured into water and the resulting solid was collected by filtration and air dried to provide 3-amino-6-(4-N-boc-amino-piperidin-1-yl)-4-propyl-thieno[2,3-b]pyridine-2-carbonitrile (847 mg, 69%).

The above nitrile (415 mg, 1.0 mmol) was suspended in 1 mL of formamide. The reaction mixture was heated in a SmithSynthesizer™ (Personal Chemistry) at 100° C. for 1 h. The reaction mixture was poured into water and the resulting solid was collected by filtration and air dried. The crude product was purified by flash chromatography (35 g silica gel cartridge, 5-10% MeOH in dichloromethane in 50 min, Rf=0.2) to give N-[1-(4-amino-9-propyl-pyrido[3',2':4,5]thieno[3,2-d]pyrimidin-7-yl)-piperidin-4-yl]-formamide as a yellow solid (249 mg, 67%).

The above formamide (249 mg, 0.672 mmol) was dissolved in 1 mL of concentrated HCl and 1 mL of water. The reaction mixture was heated in a SmithSynthesizer™ (Personal Chemistry) at 60° C. for 1 h. The solvent was removed in vacuo. The residue was recrystallized from MeOH to give a yellow solid. The solid was stirred in 5 mL of 2 M sodium carbonate solution for 6 h. The resulting yellow solid was collected by filtration, washed with water and air dried to provide the title compound (98 mg, 43%).

Example 4

Synthesis of 1-(4-amino-9-propyl-pyrido[3',2':4,5]thieno[3,2-d]pyrimidin-7-yl)-piperidin-4-one

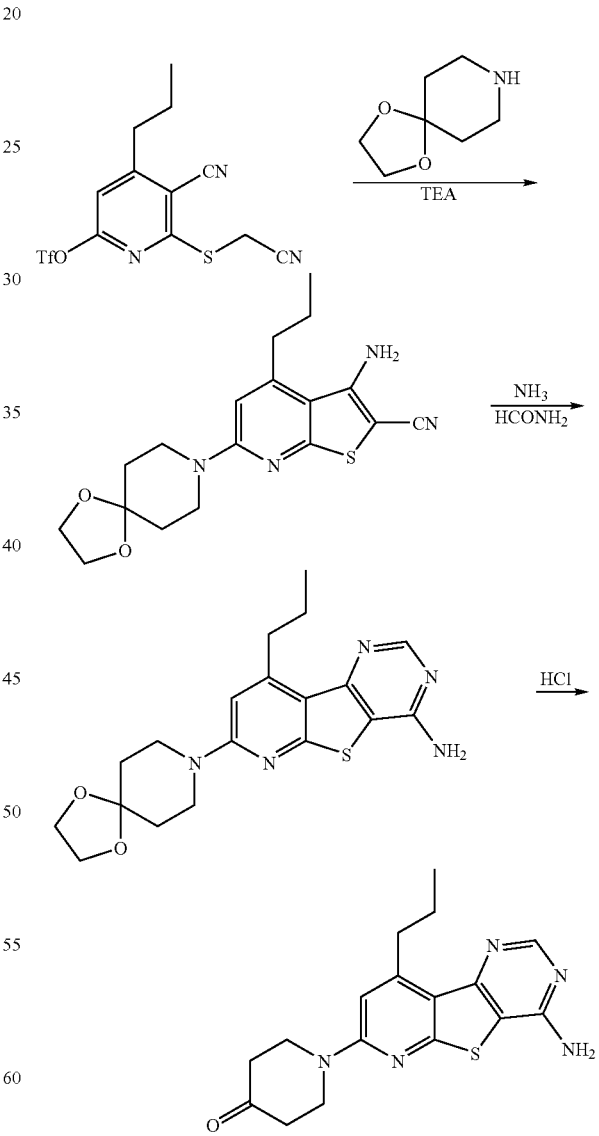

Trifluoro-methanesulfonic acid 5-cyano-6-cyanomethyl-sulfanyl-4-propyl-pyridin-2-yl ester (1.83 g, 5.00 mmol)

(see Example 1, Method B) and 1,4-dioxa-8-aza-spiro[4.5]decane (0.66 mL, 5.00 mmol) were suspended in 3 mL of dioxane. Triethylamine (0.84 mL, 6.0 mmol) was added. The reaction mixture was heated in a SmithSynthesizer™ (Personal Chemistry) at 100° C. for 2 h. The reaction mixture was poured into water and the resulting solid was collected by filtration and recrystallized from acetonitrile to give 3-amino-6-(1,4-dioxa-8-aza-spiro[4.5]dec-8-yl)-4-propyl-thieno[2,3-b]pyridine-2-carbonitrile as a yellow solid (1.57 g, 88%).

The above nitrile (1.57 g, 4.38 mmol) and formamide (3 mL), saturated with ammonia were heated in a SmithSynthesizer™ (Personal Chemistry) at 180° C. for 1 h. This reaction mixture was poured into water and the resulting solid was collected by filtration and recrystallized from MeOH to give 7-(1,4-dioxa-8-aza-spiro[4.5]dec-8-yl)-9-propyl -pyrido[3',2':4,5]thieno[3,2-d]pyrimidin-4-ylamine as a brown solid (1.13 g, 67%).

The above amine (1.13 g, 2.93 mmol) was dissolved in 3 mL of 6 M HCl. The solution was heated at 80° C. for 2 h. After cooling to room temperature, the reaction mixture was diluted with water and neutralized with sodium carbonate. The resulting precipitate was collected by filtration and recrystallized from EtOH to give the title compound as a yellow solid (0.931 g, 93%).

Example 5

Synthesis of 2-[1-(4-amino-9-propyl-pyrido[3',2':4,5]thieno[3,2-d]pyrimidin-7-yl)-piperidin-4-ylamino]-1-naphthalen-1-yl-ethanol

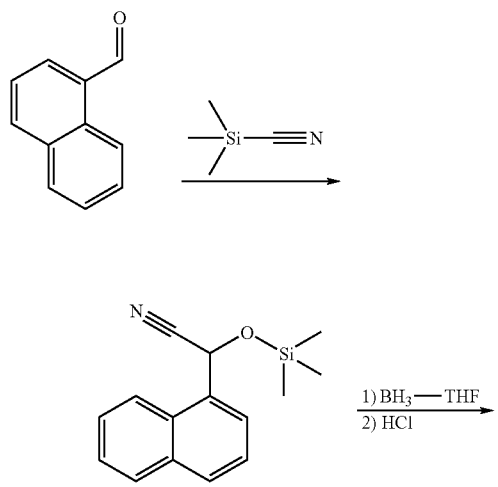

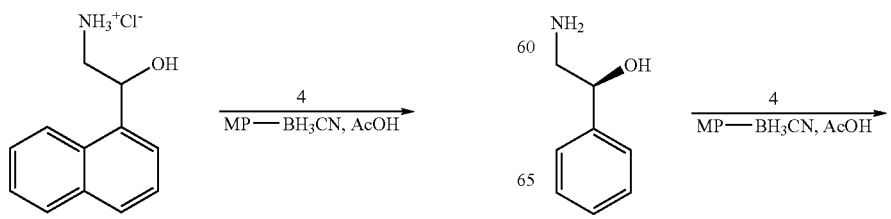

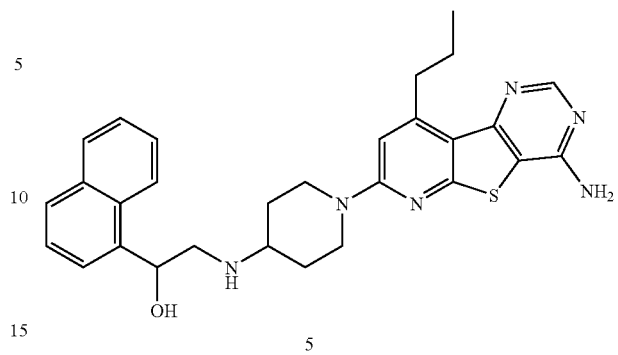

Trimethylsilyl cyanide (2.0 mL, 15 mmol) was added, dropwise, to a mixture of 1-naphthaldehyde (1.0 mL, 7.0 mmol) and Montmorillonite K 10 (0.50 g) in 40 mL of dry ether at 0° C. After stirring at room temperature for 16 h, the resulting solid was removed by filtration. The filtrate was concentrated under reduced press to give the 2.01 g of the cyanohydrin as a white solid.

The above cyanohydrin (2.01 g, 8.00 mmol) was dissolved in 30 mL of dry THF. This solution was added to a solution of boran in THF (1M, 10.0 mL, 10.0 mmol) at. 0° C. The reaction mixture was stirred at room temperature for 17 h. After quenching with MeOH, the solvent was removed in vacuo. The residue was suspended in ether, and 4 mL HCl/dioxane was added. The resulting white solid was collected via suction filtration, washed with ether, and dried in vacuo to afford 1.40 g of the amino alcohol.

The above amino alcohol (200 mg, 0.586 mmol) and 1-(4-amino-9-propyl -pyrido[3',2':4,5]thieno[3,2-d]pyrimidin-7-yl)-piperidin-4-one (Example 4) (200 mg, 0.894 mmol) was dissolved in 10 mL of dry DMF. MP-Cyanoborohydride (375 mg, 0.884 mmol) was added followed by glacial acetic acid (0.3 mL). This mixture was shaken for 16 h. The resin was removed by filtration and washed with MeOH and dichloromethane. The filtrate was evaporated. The residue was treated with 2 M sodium carbonate solution. The resulting solid was collected by filtration and recrystallized from MeOH/acetonitrile to give the title compound as a pale-colored solid. Yield: 189 mg, 63%.

Example 6

(S)-2-[1-(4-amino-9-propyl-pyrido[3',2':4,5]thieno[3,2-d]pyrimidin-7-yl) -piperidin-4-ylamino]-1-phenyl-ethanol

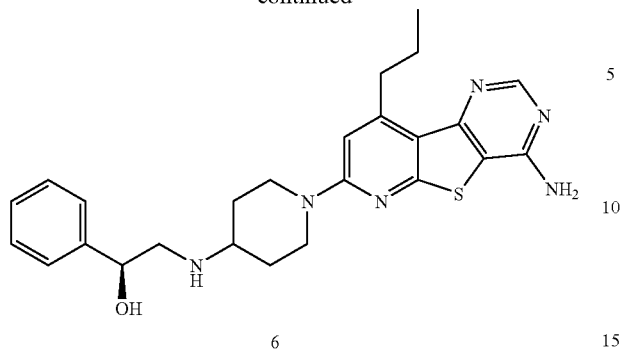

1-(4-Amino-9-propyl-pyrido[3',2':4,5]thieno[3,2-d]pyrimidin-7-yl)-piperidin-4-one (Example 4) (341 mg, 1.00 mmol) and (S)-2-amino-1-phenylethanol (142 mg, 1.00 mmol) was dissolved in 10 mL of dry DMF. MP-Cyanoborohydride (0534 mg, 1.20 mmol) was added followed by 10 drops of glacial acetic acid. This mixture was shaken for 16 h. The resin was removed by filtration and washed with MeOH and dichloromethane. The filtrate was evaporated. The residue was treated with 2 M sodium carbonate solution. The resulting solid was collected by filtration and recrystalized from MeOH/acetonitrile to give the title compound as a pale-colored solid (0.260 g, 56%).

Example 7

Synthesis of 4-{2-[1-(4-Amino-9-propyl-pyrido[3',2':4,5]thieno[3,2-d]pyrimidin-7-yl)-piperidin-4-ylamino]-1-hydroxy-ethyl}-benzamide

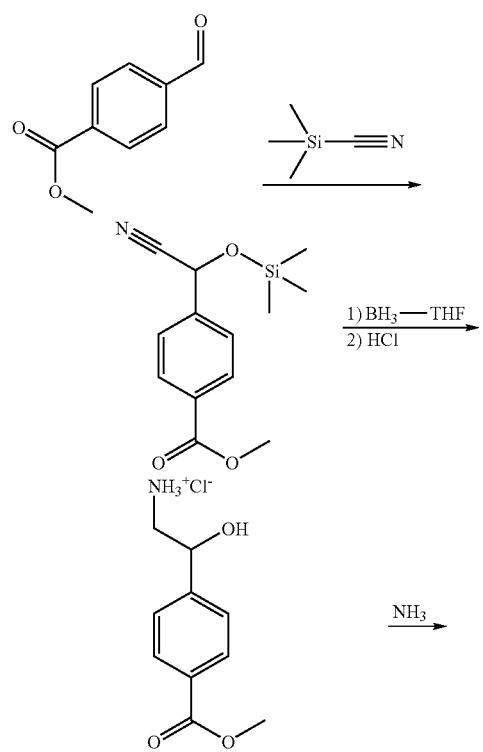

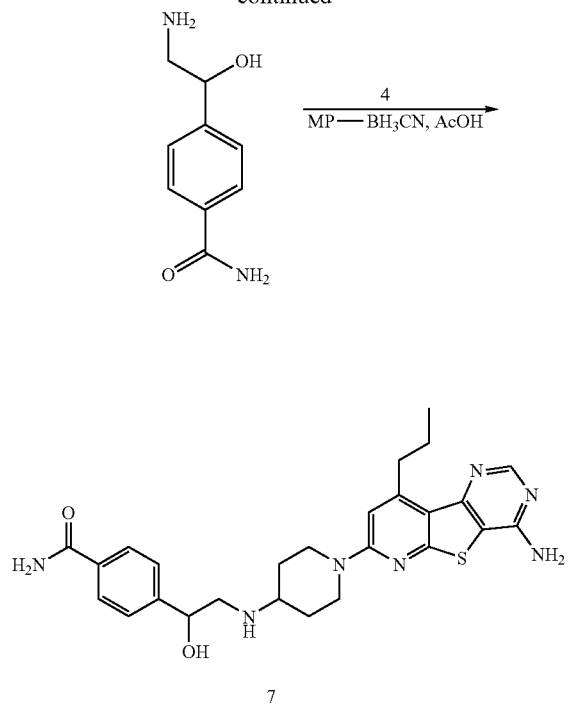

To a solution of methyl 4-formylbenzoate (15.00 g, 90.46 mmol) in 20 ML of dry diethyl ether at 0° C. was added trimethylsilyl cyanide (25.0 mL, 184 mmol) over 1 h. The resulting solid was removed by filtration. The filtrate was concentrated in vacuo to give the trimethylsilyl-protected cyanohydrin (24.05 g, 100%) as a white solid.

The above cyanohydrin (23.96 g, 90.97 mmol) was dissolved in 4 mL of dry THF. To this solution at 0° C., was added boran-THF complex (100.0 mL, 1 M, 100.0 mmol). The reaction mixture was stirred at room temperature for 16 h, cooled to 0° C. and then quenched with MeOH. The solvent was removed in vacuo and the residue was dissolved in minimum amount of EtOAc. HCl in MeOH (6 M) was added and stirred for 15 min. This mixture was diluted with 200 mL of diethyl ether. The resulting white solid was collected by filtration, washed with diethyl ether and dried in vacuo giving 18.87 g (90%) of the desired amino alcohol as the HCl salt.

The above amino alcohol HCl salt (1.00 g, 4.32 mmol) was suspended in ammonium hydroxide and heated in a stainless steel pressure vessel at 90° C. for 3 h. The solvent was removed in vacuo. The resulting free base was used without further purification. 1-(4-Amino-9-propyl-pyrido[3',2':4,5]thieno[3,2-d]pyrimidin-7-yl)-piperidin-4-one (Example 4) (570 mg, 1.67 mmol) and the above amide (300 mg, 1.67 mmol) were dissolved in 10 mL of dry DMF. MP-Cyanoborohydride (0534 mg, 1.20 mmol) was added followed by 0.5 mL of glacial acetic acid. This mixture was shaken for 16 h. The resin was removed by filtration and washed with MeOH and dichloromethane. The filtrate was evaporated. The residue was treated with 2 M sodium carbonate solution. The resulting solid was collected by filtration and purified with flash chromatography (110 g $SiO_2$, 10-20% EtOH/$CH_2Cl_2$ 1% $NH_4OH$, 50 mL/min, 100 minutes, UV detection at 254 nm) to give the title compound as a yellow solid (0.360 g, 49%).

Example 8

Synthesis of 1-(2,4-diamino-9-propyl-pyrido[3',2':4,5]thieno[3,2-d]pyrimidin-7-yl)-piperidin-4-ol

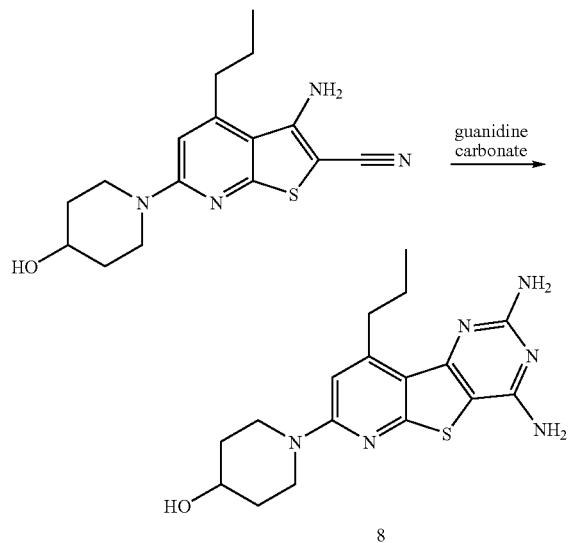

3-Amino-6-(4-hydroxy-piperidin-1-yl)-4-propyl-thieno[2,3-b]pyridine-2-carbonitrile (316 mg, 1.00 mol) (see Example 2) and guanidine carbonate (360 mg, 2 mmol) was mixed in a test tube. The mixture was heated to a melt for 15 min until the gas evolution stopped. After cooling to room temperature, the mixture purified by flash chromatography (35 g silica gel cartridge, 10% MeOH in dichloromethane, 30 mL/min for 15 min, Rf=0.25) to give the title compound as a yellow solid (120 mg, 33%).

Example 9

Synthesis of 1-(4-amino-9-propyl-pyrido[3',2':4,5]thieno[3,2-d][1,2,3]triazin-7-yl)-piperidin-4-ol

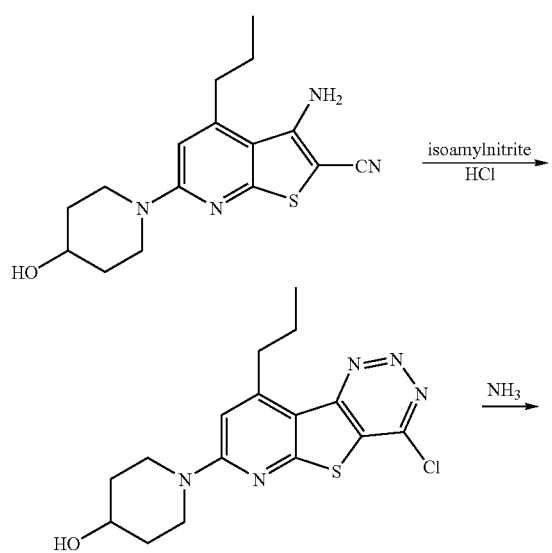

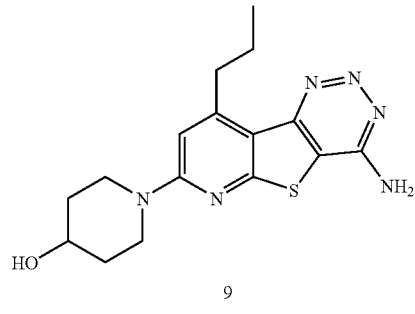

3-Amino-6-(4-hydroxy-piperidin-1-yl)-4-propyl-thieno[2,3-b]pyridine-2-carbonitrile (316 mg, 1.00 mmol) (see Example 2) was dissolved in 3 mL of HCl in EtOH (1.25 M). To this solution at 0° C. was added isoamyl nitrite (0.42 mL, 3.0 mmol). The reaction mixture was warmed up to room temperature in 2 h. The resulting precipitate was collected by filtration and washed with MeOH to give 1-(4-chloro-9-propyl-pyrido[3',2':4,5]thieno[3,2-d][1,2,3]triazin-7-yl)-piperidin-4-ol as a yellow solid (120 mg, 35%).

In a Parr steel vessel at −78° C., the above solid (170 mg, 0.467 mmol) was suspended in 3 mL of dioxane and 5 mL of liquid ammonia. The mixture was then heated in the Parr pressure vessel at 100° C. for 20 h. After cooling to −78° C., the vessel was opened and allowed to warm up to room temperature slowly. The solvent was removed in vacuo. The solid was collected by filtration and washed with water then air dried. The crude product was recrystallized from EtOH to provide the title compound (89 mg, 55%).

Example 10

Synthesis of 7-(4-amino-piperidin-1-yl)-9-trifluoromethyl-pyrido[3',2':4,5]thieno[3,2-d]pyrimidin-4-ylamine

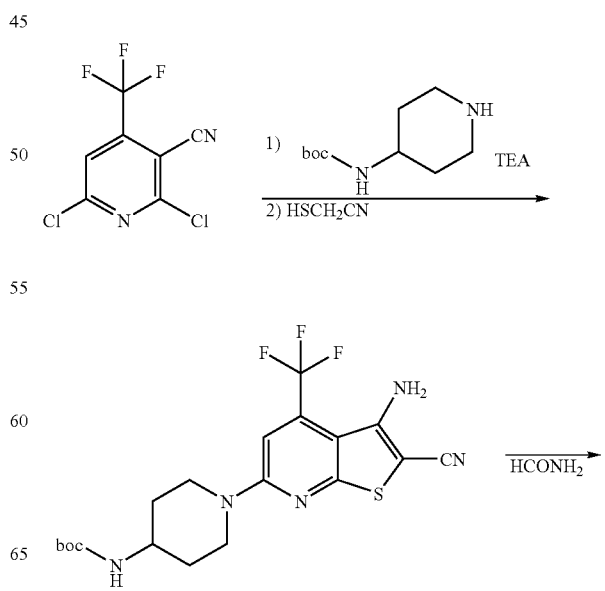

-continued

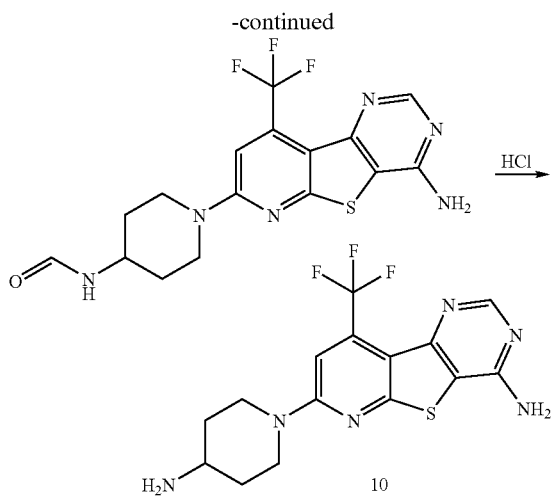

3-Cyano-2,6-dichloro-4-trifluoromethylpyridine (482 mg, 2.00 mmol) was dissolved in 10 mL of absolute EtOH. To this solution at 0° C. was added 4-N-boc-aminopiperidine (401 mg, 2.00 mmol) followed by triethylamine (0.30 mL, 2.2 mmol). This mixture was stirred at 0° C. for 1 h. A stock solution of mercaptoacetonitrile (1.2 mL, 2.4 mmol) was added followed by triethylamine (0.30 mL, 2.2 mmol). This reaction mixture was heated at 80° C. for 4 h. Water was added and the resulting solid was collected by filtration to give a yellow crystalline product (0.59 g, 67%).

The above yellow solid (500 mg, 1.13 mmol) was suspended in 3 mL of formamide saturated with ammonia. This mixture was heated at 180° C. for 2 h. After cooling to room temperature the reaction mixture was diluted with water and the resulting solid was collected by filtration and recrystallized from MeOH to give N-[1-(4-amino-9-trifluoromethyl-pyrido[3',2':4,5]thieno[3,2-d]pyrimidin-7-yl)-piperidin-4-yl]-formamide as a yellow crystalline product (288 mg, 64%).

The above yellow formamide (268 mg, 0.676 mmol) was dissolved in 3 mL of 6% HCl. This solution was heated at 80° C. for 40 min. The reaction mixture was diluted with water and neutralized with sodium carbonate to pH 10. The resulting solid was collected by filtration and recrystallized from MeOH to give the title compound as a white crystalline product (171 mg, 69%).

Example 11

Synthesis of (S)-2-[1-(8-amino-4-propyl-9-thia-1,7-diaza-fluoren-2-yl)-piperidin-4-ylamino]-1-phenyl-ethanol

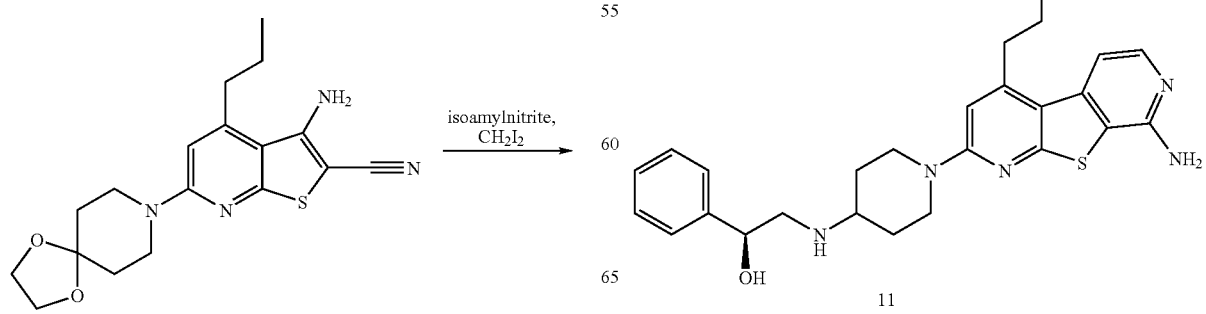

To a stirred solution of 3-amino-6-(1,4-dioxa-8-aza-spiro[4.5]dec-8-yl)-4-propyl-thieno[2,3-b]pyridine-2-carbonitrile (2.00 g, 5.58 mmol) in 7 mL of diiodomethane heated at 100° C. on an oil bath, was added isoamyl nitrite, dropwise, over 20 min. The mixture was heated for an additional hour. The mixture was cooled and fractionated directly over silica gel eluted with EtOAc/hexane (1/99 to 1/2 gradient) to give the iodo compound as a crystalline solid (0.880 g, 34%).

A mixture of the above iodo compound (0.72 g, 1.53 mmol)), bistriphenylphosphine palladium (II) chloride (0.019 g), copper (I) iodide (0.01 g), and trimethylsilylacetylene (0.4 mL) in 2 mL of DMF and triethylamine (1 mL) stirred under nitrogen, was heated at 90° C. for 2 h. The mixture was cooled to room temperature, diluted with EtOAc/hexane, washed with water, dried, filtered and evaporated. Fractionation of the residue over silica gel (EtOAc/hexane 5/95 to 3/1 gradient) gave the acetylene product as an oil (0.620 g, 92%).

To a solution of the above silylated acetylene (0.610 mg, 1.39 mmol) in THF (2 mL) was added tetrabutylammonium fluoride (1M in THF, 2.5 mL, 2.5 mmol). After 30 minutes the mixture was diluted with EtOAc, washed with water, dried, filtered, evaporated and passed through a short silica gel plug eluted with EtOAc/hexane/methylene chloride (1/1/2) to give acetylene product as a solid (0.290 g, 57%).

To a solution of the above acetylene compound (0.210 g, 0.571 mmol) in 4 mL of dioxane was added aqueous ammonium hydroxide (28%-30%, 4 mL). The mixture was divided in four equal portions in sealed screw cap thick walled test tubes. The mixtures were heated at 100° C. for 24 h. The mixtures were cooled to room temperature, combined, and diluted with EtOAc. The resulting solution was washed with water, dried, filtered and evaporated. Trituration of the residue with diethyl ether gave the ketal as a solid product which was collected by filtration (0.148 g, 67%).

The above ketal (71 mg, 18 mmol) was heated in a mixture of acetic acid (1 mL) and concentrated HCl (0.5 mL) at 100° C. in a sealed test tube for 2 h. This mixture was cooled and then added to a mixture of EtOAc and saturated aqueous sodium bicarbonate. The organic phase was separated, dried, filtered and evaporated to give solid product. The solid product was fractionated over a short column of silica gel eluted with EtOH in EtOAc (0-3%) to give the ketone as a solid product after trituration with diethyl ether (43 mg, 69%).

A mixture of the above ketone (18 mg, 13 mmol) and (S)-2-amino-1-phenyl-ethanol in 0.5 mL of EtOH with sodiumcyanoborohydride (0.009 g) was stirred at room temperature for 3 h. This mixture was diluted with chloroform, washed with water, dried, filtered and evaporated. Fractionation of the residue over deactivated basic alumina eluted with EtOH in chloroform (0-5%) gave the title compound as a solid upon tritutation with diethyl ether (4 mg, 48%).

ASSESSMENT OF BIOLOGICAL PROPERTIES

The inhibition of IKKα and IKKβ by the compounds of the present invention was determined with the following assay that measures the phosphorylation of the IκBα substrate by the respective kinases. The enzymes used in the assay were N-terminally flag-tagged versions of the human IKKβ or IKKα and the substrate was a GST fusion protein with IκBα (amino acids 1-54).

The reaction mixtures (60 μl) contained 20 mM HEPES pH 7.5, 10 mM $MgCl_2$, 2 mM $MnCl_2$, 100 mM NaCl, 100 μM $Na_3VO_4$, 20 mM β-glycerophosphate, 1 mM DTT, 2% DMSO, 250 nM ATP, 0.4 nM [$^{33}$P]ATP (specific activity, 3000 Ci/mmol), IκBα substrate, IKK enzyme and test compound. The reaction mixtures contained either 3.6 μg/ml IKKα and 245 μg/ml IκBα or 0.9 μg/ml IKKβ and 53 μg/ml IκBα.

Reactions were initiated by adding a solution of IκBα substrate and ATP to polypropylene plates containing IKK enzyme that was pre-incubated for 5 minutes with test compound. Then the reaction mixtures were incubated for 1 hour at 25° C., placed on ice and quenched by the addition of 150 μl 10% trichloroacetic acid and 5% disodium pyrophosphate. After mixing, the entire contents of the quenched reaction mixtures were transferred to a pre-wetted Packard UniFilter filtration plate, aspirated and washed 6 times with 250 μl of dd$H_2O$ using the Packard Filtermate Harvester. Filtration plates were then air dried, supplemented with 40 μl of Microscint 20 scintillation fluid and the $^{33}$P-labeled reaction products were quantified using the Packard TopCount scintillation counter.

Compounds were tested in three-fold serial dilutions and inhibitor concentrations to achieve 50% inhibition of enzyme activity (i.e., $IC_{50}$) were derived from dose-response curves using SAS software (SAS Institute, Cary N.C.). A non-linear regression analysis based on the Hill equation was applied to the percent inhibition versus concentration data. In all cases, compound concentrations were verified by HPLC.

Compounds in Table I in the Detailed Description of the Invention section were all evaluated in the assay for IKKβ inhibition and had $IC_{50}$'s of 10 μM or below. They were also evaluated for IKKα inhibition and had $IC_{50}$'s of 25 μM or below. Compounds in Table 2 had $IC_{50}$'s 1 μM or below for IKKβ inhibition.

The invention claimed is:
1. A compound of formula (III):

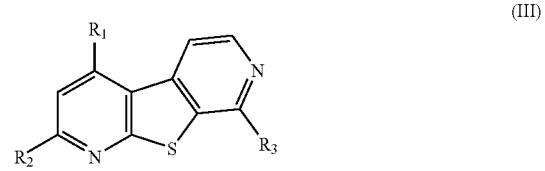

(III)

wherein:
$R_1$ is
(a) phenyl or heteroaryl selected from furanyl, thienyl, pyridyl, pyrrolyl, imidazolyl and benzofuranyl, optionally substituted with one to two $R_a$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O) heteroaryl, wherein the heteroaryl is selected from furanyl, thienyl, pyridyl and pyrrolyl,
(c) $R_b(CH_2)_mO$—,
(d) $C_{3-6}$-cycloalkyl,
(e) $C_{3-6}$-cycloalkyl$C_{1-3}$alkyl
(f) $R_bOCH_2$—,
(g) $R_b(CH_2)_mNH$—,
(h) $R_b(CH_2)_p(CH=CH)_m$—
(i) $C_{1-6}$alkyl,
(j) $C_{1-8}$alkoxy,
(k) $C_{1-8}$alkylthio,
(l) $C_{1-6}$alkoxy$C_{1-6}$alkoxy, (m) —$CF_3$,
(n) —CHO,
(o) —$OCH_2CO_2H$,
(p) —$OSO_2CF_3$,
(q) —$N(R_c)(R_d)$, or
(r) —$C(O)NR_cR_d$;

$R_2$ is
(a) $C_{1-6}$alkyl-OC(O)$C_{1-6}$alkoxy,
(b) hydroxy$C_{1-6}$alkyl-,
(c) hydroxy$C_{1-6}$alkoxy-, optionally substituted with —C(O)$C_{1-6}$alkyl,
(d) $(R_c)(R_d)NC_{1-6}$alkoxy-,
(e) $(R_c)(R_d)NC_{1-6}$alkyl-,
(f) hydroxy$C_{1-6}$alkylamino-,
(g) $(R_c)(R_d)NC_{1-6}$alkylamino-,
(h) $C_{1-6}$alkoxy$C_{1-6}$alkylamino-,
(i) heterocyclyl$(CH_2)_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$,
(j) heterocyclyl$CH_2O$— wherein the heterocyclyl is selected from 1-piperidinyl, 1-piperazinyl, 4-morpholinyl and 1-pyrrolidinyl, optionally substituted with $C_{1-6}$alkyl,
(k) $R_b(CH_2)_mO$—,
(l) heteroaryl$(CH_2)_mO$—, wherein the heteroaryl is selected from furanyl, thienyl, imidazolyl, pyridyl, indolyl and pyrrolyl,
(m) heteroaryl$C_{1-6}$alkylamino, wherein the heteroaryl is selected from furanyl, thienyl, imidazolyl, pyridyl, indolyl and pyrrolyl,
(n) —$SC_{1-6}$alkyl, or
(o) —$SC_{1-6}$alkylC(O)$N(R_c)(R_d)$;

$R_3$ is —$N(R_c)(R_d)$;

$R_a$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —$S(O)_nC_{1-6}$alkyl, —$NO_2$, —OH, —$CF_3$, —$N(R_c)(R_d)$, —$NHC(O)NHC_{1-6}$alkyl, —C(O)$N(R_c)(R_d)$ and phenyl optionally substituted with halogen, $C_{1-6}$alkyl, —CN or $C_{1-6}$alkoxy;

$R_b$ is a phenyl group optionally substituted with one or two groups selected from halogen, 1-napthyl, $C_{1-6}$alkyl, —CN, —$CO_2C_{1-6}$alkyl, —C(O)$N(R_c)(R_d)$, $NO_2$ and $C_{1-6}$alkoxy, or $R_b$ is $C_{3-6}$cycloalkyl;

$R_c$ and $R_d$ are independently selected from H, $C_{1-6}$alkyl, —C(O)$C_{1-6}$alkyl, —$SO_2C_{1-6}$alkyl, phenyl, benzyl, piperidinyl, phenylethyl and $(CH_3)_3COC(O)$—, and wherein if $R_c$ and $R_d$ are both $C_{1-6}$alkyl, they may optionally form a 4-7 member ring, together with the nitrogen they are attached to;

$R_e$ is selected from —OH, NHCHO, —$O(CH_2)$phenyl, amino, —CN, oxo-$CO_2C_{1-6}$alkyl, —$CO_2H$, —C(O)$N(R_c)(R_d)$, $N(R_c)(R_d)$, —$CH_2N(R_c)(R_d)$, —$NHCH_2CO_2H$, —$NHCH_2CO$ $N(R_c)(R_d)$, —NHCOObenzyl, $C_{1-6}$alkyl, —$CO_2$benzyl, hydroxy$C_{1-6}$ alkyl, —C(O)$C_{1-6}$alkyl$N(R_c)(R_d)$, —$NHCO_2C_{1-6}$alkyl, HOCH($R_g$)$CH_2NH$—, —NHC(O)$N(R_c)(R_d)$, —$S(O)_nC_{1-6}$alkyl, $(CH_3)_3COC(O)$—, phenyl, pyridyl, $H_2NCH(R_f)C(O)$— and —C(O)heterocyclyl, wherein said heterocyclyl is selected from piperidinyl, piperazinyl, morpholinyl and pyrrolidinyl;

$R_f$ is selected from $C_{1-6}$alkyl, —$(CH_2)_{1-4}NH_2$, benzyl or $R_b$;

$R_g$ is $C_{1-6}$alkyl, an aryl or a heteroaryl group selected from phenyl, naphthyl, imidazolyl, thienyl, thiazolyl, pyridyl, pyrimidyl, pyrazinyl, benzothiophenyl, benzothiazolyl, indolyl, benzimidazoyl, quinolinyl, isoquinolinyl, benzo[1,3]dioxoly, 2,3-dihydro-benzo[1,4]dioxinyl, 1-oxo-1,3-dihydro-isobenzofuranyl, 2,3-dihydro-benzofuranyl, 3-oxo-3,4-dihydro-2H-benzo[1,4]oxazinyl and 2-oxo-2,3-dihydro-benzooxazoly, $R_g$ is optionally substituted with one to three $R_h$ groups selected from halogen, hydroxyl, $C_{1-6}$alkyl, benzyl, $C_{1-6}$alkoxy, phenoxy, phenylamino, hydroxy$C_{1-6}$alkyl, —CN, —$CO_2H$, —$CO_2C_{1-6}$alkyl, —$N(R_c)(R_d)$, $C_{1-6}$alkyl$N(R_c)(R_d)$, —C(O)$N(R_c)(R_d)$, —$NO_2$, —$S(O)_nC_{1-6}$alkyl and —$S(O)_nN(R_c)(R_d)$, or $R_h$ is an aryl or a heteroaryl group selected from phenyl, imidazolyl, pyrazolyl, thienyl, oxazoly, thiazolyl, pyridyl, pyrimidyl, pyrazinyl, benzo[1,3]dioxoly, and quinolinyl, or $R_h$ is morpholinyl, $R_h$ is optionally substituted with one to three $R_i$ groups selected from halogen, hydroxyl, $C_{1-6}$alkyl, $C_{1-6}$alkoxy, —CN, —$CO_2H$, —$CO_2C_{1-6}$alkyl, —$N(R_c)(R_d)$ and C(O)$N(R_c)(R_d)$;

m is 0 or 1;
n is 0, 1 or 2; and
p is 0, 1, 2 or 3;

or the pharmaceutically acceptable salts, esters, isomers or tautomers thereof.

2. A compound of formula (III) as described in claim 1 wherein:

$R_1$ is
(a) phenyl or heteroaryl selected from furanyl, thienyl, pyridyl, pyrrolyl, imidazolyl and benzofuranyl, optionally substituted with one to two $R_a$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O) heteroaryl, wherein the heteroaryl is selected from furanyl, thienyl, pyridyl and pyrrolyl,
(c) $R_b(CH_2)_mO$—,
(d) $C_{3-6}$-cycloalkyl,
(e) $C_{3-6}$-cycloalkyl$C_{1-3}$alkyl
(f) $R_bOCH_2$—,
(g) $R_b(CH_2)_mNH$—,
(h) $R_b(CH_2)_p(CH=CH)_m$,—
(i) $C_{1-6}$alkyl,
(j) $C_{1-8}$alkoxy,
(k) $C_{1-8}$alkylthio,
(l) $C_{1-6}$alkoxy$C_{1-6}$alkoxy,
(m) —$CF_3$,
(n) —CHO,
(o) —$OCH_2CO_2H$,
(p) —$OSO_2CF_3$,
(q) —$N(R_c)(R_d)$, or
(r) —C(O)$NR_cR_d$;

$R_2$ is
(a) $C_{1-6}$alkyl-OC(O)$C_{1-6}$alkoxy,
(b) hydroxy$C_{1-6}$alkyl-,
(c) hydroxy$C_{1-6}$alkoxy-, optionally substituted with —C(O)$C_{1-6}$alkyl, (d) $(R_c)(R_d)NC_{1-6}$alkoxy-,
(e) $(R_c)(R_d)NC_{1-6}$alkyl-,
(f) hydroxy$C_{1-6}$alkylamino-,
(g) $(R_c)(R_d)NC_{1-6}$alkylamino-,
(h) $C_{1-6}$alkoxy$C_{1-6}$alkylamino-,
(i) heterocyclyl$(CH_2)_m$— wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$,
(j) heterocyclyl$CH_2O$— wherein the heterocyclyl is selected from 1-piperidinyl, 1-piperazinyl, 4-morpholinyl and 1-pyrrolidinyl, optionally substituted with $C_{1-6}$alkyl,
(k) $R_b(CH_2)_mO$—,
(l) heteroaryl$(CH_2)_mO$—, wherein the heteroaryl is selected from furanyl, thienyl, imidazolyl, pyridyl, indolyl and pyrrolyl,
(m) heteroaryl$C_{1-6}$alkylamino, wherein the heteroaryl is selected from furanyl, thienyl, imidazolyl, pyridyl, indolyl and pyrrolyl,
(n) —$SC_{1-6}$alkyl, or
(o) —$SC_{1-6}$alkyl$C(O)N(R_4)(R_5)$;
$R_3$ is —$N(R_c)(R_d)$;
$R_a$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —$S(O)_nC_{1-6}$alkyl, —$NO_2$, —OH, —$CF_3$, —$N(R_c)(R_d)$, —$NHC(O)NHC_{1-6}$alkyl, —$C(O)N(R_c)(R_d)$ and phenyl optionally substituted with halogen, $C_{1-6}$alkyl, —CN or $C_{1-6}$alkoxy;
$R_b$ is a phenyl group optionally substituted with one or two groups selected from halogen, 1-naphtyl, $C_{1-6}$alkyl, —CN, —$CO_2C_{1-6}$alkyl, —$C(O)N(R_c)(R_d)$, $NO_2$ and $C_{1-6}$alkoxy, or $R_b$ is $C_{3-6}$cycloalkyl,
$R_c$ and $R_d$ are independently selected from H, $C_{1-6}$alkyl, —$C(O)C_{1-6}$alkyl, —$SO_2C_{1-6}$alkyl, phenyl, benzyl, piperidinyl, phenylethyl and $(CH_3)_3COC(O)$—;
$R_e$ is selected from —OH, —NHCHO, $O(CH_2)$phenyl, amino, —CN, oxo, —$CO_2C_{1-6}$alkyl, —$CO_2H$, —$C(O)N(R_c)(R_d)$, —$N(R_c)(R_d)$, —$CH_2N(R_c)(R_d)$, —$CH_2OH$, $C_{1-6}$alkyl, —$CO_2$benzyl, hydroxy$C_{1-6}$alkyl, —$C(O)C_{1-6}$alkylN$(R_c)(R_d)$, —$NHCO_2C_{1-6}$alkyl, HOCH$(R_b)$$CH_2NH$—, —$NHC(O)N(R_c)(R_d)$, —$S(O)_nC_{1-6}$alkyl, $(CH_3)_3COC(O)$—, phenyl, pyridyl, HNCH$(R_f)C(O)$— and —$C(O)$heterocyclyl, wherein said heterocyclyl is selected from piperidinyl, piperazinyl, morpholinyl and pyrrolidinyl;

$R_f$ is selected from $C_{1-6}$alkyl, —$(CH_2)_{1-4}NH_2$, phenyl or benzyl;
m is 0 or 1;
n is 0, 1 or 2; and
p is 0, 1, 2 or 3;
or the pharmaceutically acceptable salts, esters, isomers or tautomers thereof.

3. A compound of formula III of claim 2 wherein:
$R_1$ is
(a) $C_{1-6}$alkyl,
(b) $C_{1-4}$alkoxy,
(c) $C_{3-6}$-cycloalkyl,
(d) $C_{3-6}$-cycloalkyl$C_{1-3}$alkyl
(e) $C_{1-4}$alkylthio,
(f) —$CF_3$, or
(g) —$C(O)NR_cR_d$;
$R_2$ is
heterocyclyl wherein said heterocycle is selected from 1-piperidinyl, 1-piperazinyl, 4-morpholinyl, 1-azepanyl, 1-pyrrolidinyl, diazepan-1-yl, 1,4-diazacycloheptan-1-yl, and 2,5-diazabicyclo[2.2.1]heptan-2-yl, and is optionally substituted with one or two $R_e$,
$R_3$ is —$NH_2$;
$R_c$ and $R_d$ are independently selected from H, $C_{1-6}$alkyl, —$C(O)C_{1-4}$alkyl, —$SO_2C_{1-6}$alkyl, phenyl, benzyl, piperidinyl, phenylethyl and $(CH_3)_3COC(O)$—;
$R_e$ is selected from —OH, —$NH_2$, —NHCHO, —$O(CH_2)$phenyl, amino, —CN, oxo, —$CO_2C_{1-6}$alkyl, —$CO_2H$, —$C(O)N(R_c)(R_d)$, —$N(R_c)(R_d)$, —$CH_2N(R_c)(R_d)$, —$CH_2OH$, $C_{1-6}$alkyl, —$CO_2$benzyl, hydroxy$C_{1-6}$alkyl, —$C(O)C_{1-6}$alkylN$(R_c)(R_d)$, —$NHCO_2C_{1-6}$alkyl, HOCH$(R_b)CH_2NH$—, —$NHC(O)N(R_c)(R_d)$, —$S(O)_nC_{1-6}$alkyl, $(CH_3)_3COC(O)$—, phenyl, pyridyl, $H_2NCH(R_f)C(O)$— and —$C(O)$heterocyclyl, wherein said heterocyclyl is selected from piperidinyl, piperazinyl, morpholinyl and pyrrolidinyl;
$R_f$ is selected from $C_{1-6}$alkyl, —$(CH_2)_{1-4}NH_2$, phenyl or benzyl;
m is 0 or 1;
n is 0, 1 or 2; and
p is 0, 1, 2 or 3;
or the pharmaceutically acceptable salts, esters, isomers or tautomers thereof.

4. A compound chosen from:

| Compound No. | Name | Structure |
|---|---|---|
| 1. | 1-(8-Amino-4-propyl-9-thia-1,7-diaza-fluoren-2-yl)-piperidin-4-one | 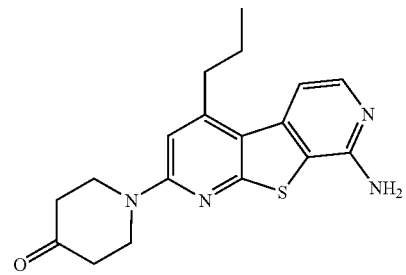 |

-continued

| Compound No. | Name | Structure |
|---|---|---|
| 2. | (S)-2-[1-(8-Amino-4-propyl-9-thia-1,7-diaza-fluoren-2-yl)-piperidin-4-ylamino]-1-phenyl-ethanol | | and pharmaceutically acceptable derivatives thereof.

5. A pharmaceutical composition comprising a pharmaceutically effective amount of a compound according to claim 1 and one or more pharmaceutically acceptable carriers and/or adjuvants.

6. A pharmaceutical composition comprising a pharmaceutically effective amount of a compound according to claim 2 and one or more pharmaceutically acceptable carriers and/or adjuvants.

7. A pharmaceutical composition comprising a pharmaceutically effective amount of a compound according to claim 3 and one or more pharmaceutically acceptable carriers and/or adjuvants.

8. A pharmaceutical composition comprising a pharmaceutically effective amount of a compound according to claim 4 and one or more pharmaceutically acceptable carriers and/or adjuvants.

* * * * *